US008859225B2

(12) United States Patent
Harjes et al.

(10) Patent No.: US 8,859,225 B2
(45) Date of Patent: Oct. 14, 2014

(54) SYSTEMS AND METHODS OF VOLTAGE-GATED ION CHANNEL ASSAYS

(75) Inventors: Daniel I. Harjes, Cambridge, MA (US); Heather A. Clark, Lexington, MA (US)

(73) Assignee: The Charles Stark Draper Laboratory, Inc., Cambridge, MA (US)

(*) Notice: Subject to any disclaimer, the term of this patent is extended or adjusted under 35 U.S.C. 154(b) by 1306 days.

(21) Appl. No.: 12/579,983

(22) Filed: Oct. 15, 2009

(65) Prior Publication Data

US 2010/0105075 A1 Apr. 29, 2010

Related U.S. Application Data

(62) Division of application No. 11/507,956, filed on Aug. 22, 2006, now abandoned.

(60) Provisional application No. 60/838,647, filed on Aug. 17, 2006.

(51) Int. Cl.
| | | |
|---|---|---|
| *C12Q 1/02* | (2006.01) | |
| *C12Q 1/04* | (2006.01) | |
| *C12Q 1/00* | (2006.01) | |
| *C12N 5/00* | (2006.01) | |
| *C12N 5/02* | (2006.01) | |
| *C12Q 1/18* | (2006.01) | |
| *G01N 21/80* | (2006.01) | |
| *G01N 33/84* | (2006.01) | |
| *C12N 13/00* | (2006.01) | |
| *G01N 21/64* | (2006.01) | |
| *C12Q 1/54* | (2006.01) | |
| *G01N 33/567* | (2006.01) | |
| *G01N 33/53* | (2006.01) | |

(52) U.S. Cl.
CPC ............ *G01N 21/6428* (2013.01); *G01N 21/80* (2013.01); *G01N 33/84* (2013.01); *C12N 13/00* (2013.01); *G01N 21/6452* (2013.01); *Y10S 435/808* (2013.01)
USPC ................ 435/29; 435/4; 435/7.2; 435/14; 435/325; 435/808

(58) Field of Classification Search
USPC .......................... 435/4, 7.2, 14, 29, 325, 808
See application file for complete search history.

(56) References Cited

U.S. PATENT DOCUMENTS

| | | | |
|---|---|---|---|
| 4,272,484 A | 6/1981 | Lubbers | |
| 4,272,485 A | 6/1981 | Lubbers | |
| 4,379,041 A | 4/1983 | Petranek et al. | |
| 4,945,171 A | 7/1990 | Haugland et al. | |
| 5,057,431 A | 10/1991 | Lubbers et al. | |
| 5,128,019 A | 7/1992 | Karpf et al. | |
| 5,132,095 A | 7/1992 | Koshiishi et al. | |
| 5,494,640 A | 2/1996 | Simon et al. | |
| 5,691,205 A | 11/1997 | Kawabata et al. | |
| 5,908,624 A | 6/1999 | Scott et al. | |
| 6,057,114 A | 5/2000 | Akong et al. | |
| 6,143,558 A | 11/2000 | Kopelman et al. | |
| 6,143,570 A | 11/2000 | Alder et al. | |
| 6,379,955 B1 | 4/2002 | Kopelman et al. | |
| 6,699,465 B2 | 3/2004 | Scott | |
| 6,969,449 B2 | 11/2005 | Maher et al. | |
| 7,704,407 B2 | 4/2010 | Makino et al. | |
| 2002/0155600 A1 | 10/2002 | Kopelman et al. | |
| 2003/0157535 A1 | 8/2003 | Berkovic | |
| 2003/0213691 A1 | 11/2003 | Peper et al. | |
| 2003/0217920 A1 | 11/2003 | Peper et al. | |
| 2004/0048390 A1 | 3/2004 | Wang et al. | |
| 2004/0058384 A1 | 3/2004 | Bakker et al. | |
| 2004/0058458 A1 | 3/2004 | Anker et al. | |
| 2004/0115614 A1 | 6/2004 | Burnett et al. | |
| 2004/0146944 A1 | 7/2004 | Fang et al. | |
| 2004/0191757 A1 | 9/2004 | Maher et al. | |
| 2005/0011760 A1 | 1/2005 | Bakker et al. | |
| 2006/0003310 A1 | 1/2006 | Klauke et al. | |
| 2006/0008924 A1 | 1/2006 | Anker et al. | |
| 2006/0013543 A1 | 1/2006 | Walt et al. | |
| 2006/0083688 A1 | 4/2006 | Singaram et al. | |
| 2006/0121446 A1 | 6/2006 | Abassi et al. | |
| 2006/0148104 A1 | 7/2006 | Marini et al. | |
| 2007/0107625 A1 | 5/2007 | Anderson et al. | |
| 2008/0131909 A1 | 6/2008 | Clark et al. | |
| 2009/0155183 A1 | 6/2009 | Clark | |
| 2010/0041067 A1* | 2/2010 | Clark | .............................. 435/7.2 |
| 2010/0221188 A1 | 9/2010 | Clark et al. | |
| 2010/0227334 A1 | 9/2010 | Clark | |

FOREIGN PATENT DOCUMENTS

| | | |
|---|---|---|
| WO | WO-99/45357 | 9/1999 |
| WO | WO-01/08660 | 2/2001 |
| WO | WO-2004/083902 | 9/2004 |

(Continued)

OTHER PUBLICATIONS

Morf et al. Carriers for chemical sensors: Design features of optical sensors (optodes) based on selective chromoionophores. Pure & Appl. Chem. 61:9, 1613-18 (1989).
Morf et al. Design of a Calcium-Selective Optode Membrane Based on Neutral Ionophores. Anal. Chem. 62:738-42 (1990).
Lerchi et al. Lead-Selective bulk Optodes Based on Neutral Ionophores with Subnanomolar Detection Limits. Anal. Chem. 64: 1534-40. (1992).
Chan, W.H. et al. Potassium Ion-selective Optodes Based on the Calix[6]arene Hexaester and Application in Human Serum Assay. Analyst. 121: 531-34 (1996).
Wang, K. et al. Characterization of Potassium-Selective Optode Membranes Based on Neutral Ionophores and Application in Human Blood Plasma. Anal. Sci. 6:5, 715-20 (1990).

(Continued)

*Primary Examiner* — Jon P Weber
*Assistant Examiner* — Kailash C Srivastava
(74) *Attorney, Agent, or Firm* — Foley & Lardner LLP; Edward A. Gordon

(57) ABSTRACT

Systems and methods are provided for optically measuring ion concentrations in biological samples. The systems and methods employ polymer-based optical ion sensors that include ion-selective ionophores and a pH sensitive chromionophore. Electrodes are providing for electrically stimulating the biological samples.

24 Claims, 16 Drawing Sheets

(56) References Cited

FOREIGN PATENT DOCUMENTS

| WO | WO-2006/050257 | 5/2006 |
|---|---|---|
| WO | WO-2007/054689 A1 | 5/2007 |
| WO | WO-2007/067733 | 6/2007 |
| WO | WO-2007/067743 A2 | 6/2007 |
| WO | WO-2008/016646 A2 | 2/2008 |
| WO | WO-2008/063151 | 5/2008 |
| WO | WO-2008/153930 | 12/2008 |
| WO | WO-2009/051703 | 4/2009 |

OTHER PUBLICATIONS

Johnson, R.D. et al. Development of a Fully Integrated Analysis System for Ions Based on Ion-Selective Optodes and Centrifugal Microfluidics. Anal. Chem. 73: 3940-46 (2001).
Seiler, K. et al. Characterization of Sodium-Selective Optode Membranes Based on Neutral Ionophores and Assay of Sodium in Plasma. Clin. Chem. 37:8, 1350-55 (1991).
Lerchi et al. Bulk Optodes Based on Neutral Dithiocarbamate Ionophores with High Selectivity and Sensitivity for Silver and Mercury Cations. Anal. Chem. 66:10, 1713-17 (1994).
Office Action mailed Apr. 21, 2009 for U.S. Appl. No. 11/507,956.
Arimori et al., "A D-glucose Selective Fluorescent Assay," Tetrahedron Letters, 43:303-305 (2002).
Barker et al., "Radiometric and Flourescense—Lifetime-Based Biosensor IncorporatingCytochrom C'and the Detection of Extra- and Intracellular Macrophage Nitric Oxide," AnalChem, vol. 71, No. 9, May 1, 1999, pp. 1767-1772.
Brasuel et al. Fluorescent Nanosensors for Intracellular Chemical Analysis: Decyl Methacrylate Liquid Polymer Matrix and Ion-Exchange-Based Potassium PEBBLE Sensors with Real-Time Application to Viable Rat C6 Glioma Cells, Anal Chem 2001 vol. 73, pp. 2221-2228.
Bruchez et al., "Semiconductor Nanocrystals as Fluorescent Biological Labels," Science 281:2013-2016 (1998).
Buck et al., "Nanoscale Probes Encapsulated by Biologically Localized Embedding (PEBBLEs) for Ion Sensina and Imaaina in Live Cells," Talanta, vol. 63, No. 1, May 10, 2004, pp. 41-59.
Buehlmann et al., "Carrier-Based Ion-Selective Electrodes and Bulk Optodes. 2. Ionophores for Potentiometric and Optical Sensors," Chem Rev, vol. 98, Jan. 1, 1998, pp. 1593-1687.
Chen et al., Lighting up cancer cells with "dots", The Lancet, 364: 2001-2003 (2004).
Clapp, et al., "Quantum Dot-Based Multiplexed Fluorescence Resonance Energy Transfer," J. Am. Chem. Soc., 127:18212-18221 (2005).
Clark, H. A., et al. "Optochemical Nanosensors and Subcellar Applications in Living Cells" Mikrochimica Acta, 131(1/02) 121-128 (1999).
International Search Report, PCT/US2008/017726, dated Mar. 16, 2009.
Dubach, et al., "Ion-Selective Nano-optodes Incorporating Quantum Dots," J. Am. Chem. Soc., 129(27), 8418-8419, (2007).
Dubach, J. M. et al., "Fluorescent Ion-Selective Nanosensors for Intracellular Analvsis with Improved Lifetime and Size" Nano Letters, 7(6):1827-1831 (2007).
European Search Report for EP Appln No. 06851882.8, mailed Mar. 31, 2009.
Examination Report mailed Mar. 11, 2010 in EP Appln No. 06851882.8.
Garg et al., "Micropigmentation: Tattooing for Medical Purposes", Dermatol. Surg. 31 :928-31 (2005).
Goldman, et al., "Multiplexed Toxin Analysis Using Four Colors of Quantum Dot Fluororeagents," Analytical Chemistry, 76(3):684-688 (2004).
International Search Report for PCT Application No. PCT/US2006/036040, mailed Aug. 29, 2008, 4 pages.
Jia et al., "A Method to Construct a Third-Generation Horseradish Peroxidase Biosensor: Self-Assembling Gold nanoparticles to Three-Dimensional Sol-Gel Network," Anal. Chem 74: 2217-2223 (2002).
Kohls et al., "Setup of a Fiber Optical Oxygen Multisensor-System and its Applications in Biotechnology," Sensors Actuators B, vol. 70, No. 1-3, Nov. 1, 2000.
Kulcu et al., "Physiological Differences Between Interstitial Glucose and Blood Glucose Measured in Human Subjects", Diabetes Care, 26(8):2405-09 (2003).
McGraw-Hili Dictionary of Scientific and Technical Terms, Sixth Edition, p. 1633, Published 2003.
Nagai et al., "Circularly permuted green fluorescent proteins engineered to sense Ca2+", PNAS, 98(6):3197-3202 (2001).
Notice of Allowance in U.S. Appl. No. 11/522,169 dated May 17, 2012.
Office Action in U.S. Appl. No. 12/584,528 dated May 21, 2012.
PCT/US2009/005065 International Search Report dated Feb. 15, 2010.
Puntener et al., "Improving the lower detection limit of potentiometric sensors by covalently binding the ionophore to a polymer backbone," Analytica Chimica Acta, 503: 187-194 (2004).
Ruedas-Rama, et al., "A multi-ion particle sensor," Chem. Commun. (Camb), 15:1544-1546 (2007).
Russell et al., "A Fluorescence-Based Glucose Biosensor Using Concanavalin A and Dextran Excapsulated in a Poly( ethylene glyco) Hydrogel," Anal. Chem. 71 :3126-3132 (1999).
Schmidtke et al., "Measurement and Modeling of the Transient Difference Between Blood and Subcutaneous Glucose Concentrations in the Rat After Injection of Insulin", Proc. Natl. Acad. Sci. USA, 95:294-99 (1998).
Sigworth et al., "Microchip Technoloyg in Ion-Channel Research," IEEE Trans Nanobiosci, vol. 4, No. 1, Mar. 1, 2005, pp. 121-127.
Snee, et al., "A Ratiometric CdSe/ZnS Nanocrystal pH Sensor," J. Am. Chem. Soc., 128(41):13320-13321 (2006).
Springsteen et al., "Alizarin Red S. as a general optical reporter for studying the binding of boronic acids with carbohydrates", The Royal Society of Chemistry 17: 1608-1609 (2001).
Tamada et al., "Noninvasive Glucose Monitoring Comprehensive Clinical Results", JAMA, 282(19):1839-44 (1999).
US Notice of Allowance on May 9, 2012.
Written Opinion for PCT Application No. PCT/US2006/036040, mailed Aug. 29, 2008, 7 paqes.
Written Opinion mailed Mar. 16, 2009 in PCT Application No. PCT/US2008/011726.
Xu, et al., "Multicolor Quantum Dot Encoding for Polymeric Particle-Based Optical Ion Sensors," Analytical Chemistry, vol. 79, No. 10, pp. 3716-3723 (2007).

* cited by examiner

SYSTEMS AND METHODS OF VOLTAGE-GATED ION CHANNEL ASSAYS

REFERENCE TO RELATED APPLICATIONS

This application is a divisional of U.S. patent application Ser. No. 11/507,956 entitled "Systems and Methods of Voltage-Gated Ion Channel Assays" filed on Aug. 22, 2006, which claims the benefit of U.S. Provisional Application No. 60/838,647, entitled, "High Throughput Optical Sensor Arrays for Drug Screening," filed on Aug. 17, 2006, the entire contents of which are hereby incorporated by reference.

BACKGROUND OF THE INVENTION

Electrically stimulated voltage-gated ion channels control many of the most basic functions in the human body, including the contraction of muscle cells and the propagation of nervous system signals via muscle and nerve cells. Various compounds are known to interfere with the proper operation of these voltage-gated ion channels.

SUMMARY OF THE INVENTION

In one aspect, the invention relates to a cell assay system suitable for observing the impact of agents on the functioning of voltage-gated ion channels in electrically stimulated cells. In one embodiment the cell assay system includes a post that has a distal end sized for introduction into a biological sample holder and a plurality of electrodes for generating an electric field between the electrodes when introduced into the biological sample holder. At least one of the electrodes is coupled to the post. In addition, a polymer-based optical ion sensor is positioned proximate the distal end of the post. The optical ion sensor includes at least one ionophore for selectively binding a predetermined ion and one pH-sensitive chromionophore. The binding of the predetermined ion alters the pH of the optical ion sensor. The chromionophore optically indicates the concentration of the predetermined ion based on the pH of the optical ion sensor and the resulting fluorescence of the chromionophore.

The optical ion sensor can take a number of forms. In one embodiment, the optical ion sensor is removably coupled to the post, for example, as a removable insert. Alternatively, the optical ion sensor can be coupled to the biological sample holder or it may be suspended in a fluid in the biological sample holder. In still other embodiments, the optical ion sensor is a particle inside of a cell in the biological sample holder. The optical ion sensor can be introduced into the cell through a variety of means including injection, endocytosis, or phagocytosis. In still other implementations, one optical ion sensor is coupled to the post or otherwise maintained outside of a cell and a second optical ion sensor is introduced into the cell. In implementations with two optical ion sensors, the optodes may have ionophores selective for different target ions and/or they may have chromionophores that have distinct fluorescence properties so that the system can simultaneous indicate the concentration of two different ions.

In various embodiments, the cell assay system also includes a controllable voltage source for generating a voltage across the electrodes. The voltage can be period or constant. In one implementation, the voltage source can generate a voltage high enough to electroporate a cell. The controllable voltage source also may provide a voltage sufficient to activate an ion channel in a cell.

In one embodiment, the cell assay system includes a means for introducing an agent into the biological sample holder, such as a hole through which an agent may be dispensed, a pipette, or a electromechanical dispenser. The electromechanical dispenser, in one particular implementation includes a solenoid.

In one embodiment, the electrodes are two parallel electrodes coupled to opposing portions of the post. Alternatively, the electrodes may be coaxial. In still other embodiments, at least one electrode is coupled to the biological sample holder. The electrodes may be transparent, reflective, or opaque. In one particular embodiment, the cell assay system includes two pairs of opposing electrodes, which are perpendicular to one another.

The cell assay system may also include a light source and a light sensor. A computing device may include modules for controlling each. The light sensor detects and measures the fluorescence of the optical ion sensors. The computing device may also include an analysis module for analyzing the output of the light sensor, a voltage control module for controlling the voltage source, and an agent introduction module for controlling the agent introduction means. The analysis module, in one embodiment, compares the output of the light sensor before an introduction of an agent into the biological sample holder to the output of the light sensor after the introduction of the agent into the biological sample holder.

In another aspect, the invention relates to a cell assay system that includes an array of posts having optical ion sensors, such as those described above, positioned proximate thereto. The optical ion sensors corresponding to each posts may be the selective for the same ions or the they may be selective for different ions. The cell assay system also includes a plurality of electrode sets corresponding to the array of posts. The electrode sets are configured to generate an electric field when introduced into a corresponding biological sample holder in an array of biological sample holders. The array of biological sample holders, in one embodiment is a standard 6-well, 12-well, 24-well, 48-well, 96-well, 384-well, and a 1534-well plate.

In one embodiment, the cell assay system includes a computing device including an agent introduction control module for controlling the introduction of an agent into at least one of the biological sample holders. The agent introduction control module controls the introduction of a plurality of agents into respective ones of the biological sample holders in the array of biological sample holders. The computing device may also include an analysis module for comparing the fluorescence of the plurality of optical ion sensors before an introduction of at least one agent into at least one of the respective biological sample holders to the fluorescence of the corresponding plurality of optical ion sensors after the introduction of the at least one agent into the respective biological sample holders.

An additional feature of the cell assay system is a robotics module for robotically introducing the array of posts into the array of biological sample holders. The robotics module may also configured to introduce the array of posts into a plurality of arrays of biological sample holders in sequence.

In another aspect, the invention relates to a method of conducting a biological assay. The method includes introducing a polymer-based optical ion sensor into a biological sample holder. The optical ion sensor includes at least one ionophore for selectively binding a predetermined ion and one pH-sensitive chromionophore. The binding of the predetermined ion alters the pH of the optical ion sensor. The chromionophore optically indicates the concentration of the predetermined ion based on the pH of the optical ion sensor and the resulting fluorescence of the chromionophore. The method also includes generating an electric field across a cell in the biological sample holder, and measuring an output of a light sensor monitoring a fluorescence of the optical ion sensor in response to the generation of the electric field. The method, in one embodiment includes varying the electric field. Additional features include introducing an agent into the biological sample holder and detecting a change in the output of the light sensor in response to the introduction of the agent.

In addition, based on a detected change, the method, in one embodiment, determines that the agent is toxic. For example, the method may determine whether the agent is a nerve or heart toxin. Alternatively, the method may determine that the agent is a candidate for treating a condition or illness. Diseases or conditions known to be related to voltage-gated ion channels include, for example, Central core disease, Hyperkalemic periodic paralysis, paramyotonia congenita, and potassium-aggravated myotonia, Hypokalemic periodic paralysis, Malignant hyperthermia, Myotonia congenita, Long Q-T syndrome, Generalized epilepsy with febrile seizures, Episodic ataxia type 1, Hemiplegic migraine and allelic ataxias, X-linked congenital stationary night blindness, Human Bartter Syndrome, and Human X-Linked Recessive Nephrolithiasis. In another implementation, the method may identify the agent by comparing it to fluorescence fingerprints of known agents.

In a further aspect, the invention relates to another method of conducting a biological assay in which an array of biological sample holders are provided. The method includes introducing an array of polymer-based optical ion sensors, such as those described above, into biological sample holders in the array of biological sample holders. Electric fields are generated across cells in the biological sample holders in the array of biological sample holders. The output of a light sensor monitoring the fluorescence is then measured to observe the response of the optical ion sensors to the electric fields. The method, in one embodiment, includes introducing a first agent into one of the biological sample holders in the array of biological sample holders, and introducing a second agent into a second of the biological sample holders in the array of biological sample holders. The method may also include detecting a change in the output of the light sensor resulting from the introduction of the first and second agents. In still another embodiment, the invention includes providing a second array of biological sample holders and robotically introducing the array of optical ion sensors into the second array of biological sample holders.

BRIEF DESCRIPTION OF THE DRAWINGS

The invention may be better understood from the following illustrative description with reference to the following drawings.

DESCRIPTION OF CERTAIN ILLUSTRATIVE EMBODIMENTS

To provide an overall understanding of the invention, certain illustrative embodiments will now be described, including methods and systems for optical evaluation of ion concentrations in biological samples. However, it will be understood by one of ordinary skill in the art that the methods and systems described herein may be adapted and modified as is appropriate for the application being addressed and that the systems and methods described herein may be employed in other suitable applications, and that such other additions and modifications will not depart from the scope hereof.

Figure 1:
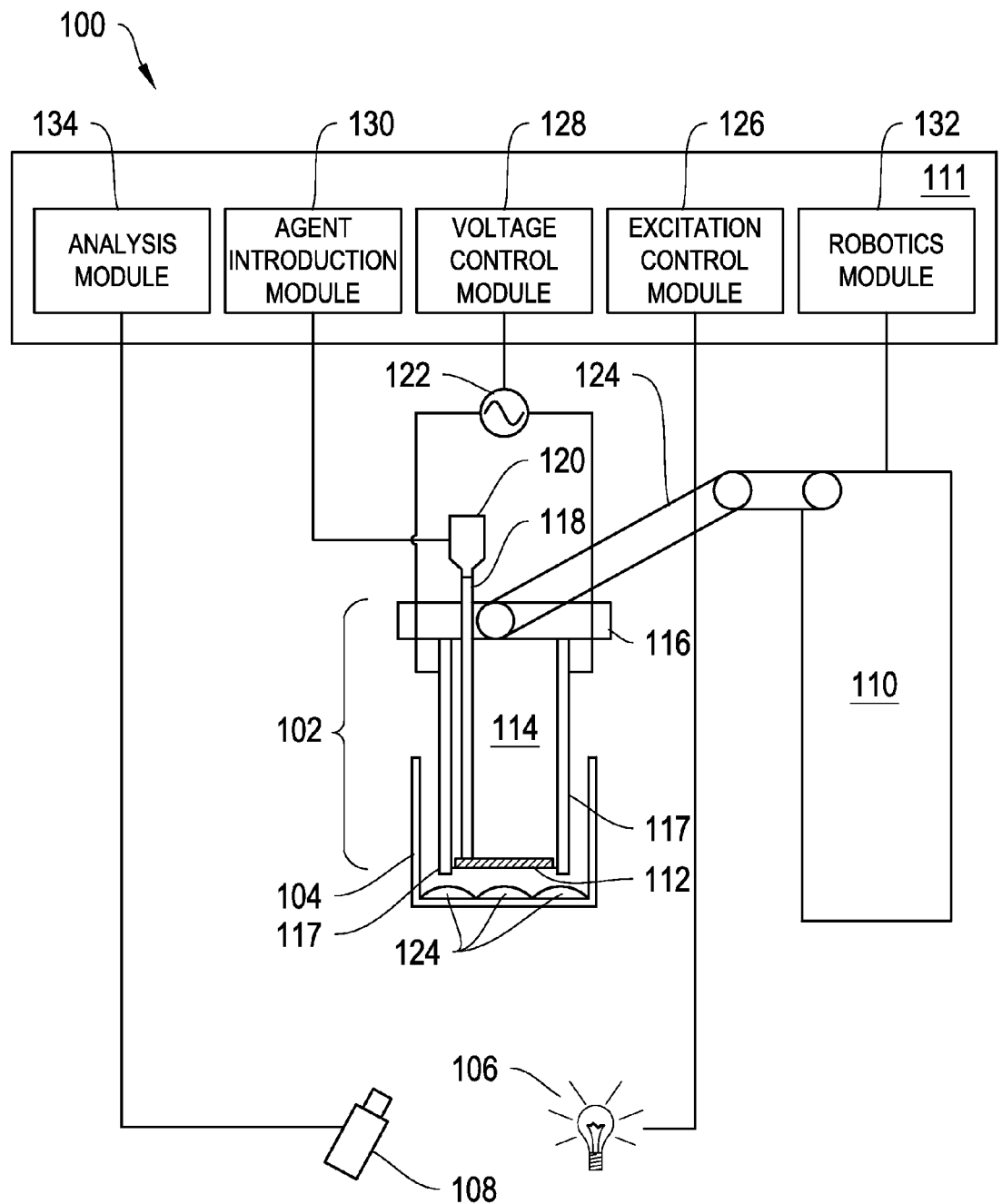
FIG. 1 is a schematic diagram of a cell assay system according to an illustrative embodiment of the invention.

FIG. 1 is a schematic diagram of a cell assay system 100 according to an illustrative embodiment of the invention. The cell assay system 100 includes an optical ion sensor support 102, a biological sample holder 104, an excitation light source 106, a light sensor 108, a robotics assembly 110, and a computing device 111.

The optical ion sensor support 102 supports an optical ion sensor 112 for positioning in the biological sample holder 104. In the illustrative embodiment, the optical ion sensor support 102 take the form of a post 114 extending from a platform 116, which is coupled to the robotics assembly 111. The post can be of any material which is compatible with the optical ion sensor 112. In various implementations, the optical ion sensor 112 is adhered to the optical ion sensor support 102 by depositing onto the distal end of the post 114 a solution of optical ion sensor matrices dissolved in a solvent, such as in a polar organic solvent like Tetrahydrofuran (THF). In such implementations, the post is preferably formed from a material resistant to the solvent. Materials resistant to THF include, without limitation, 304 stainless steel, 316 stainless steel, Acetal polymer (marketed as DELRIN™ by E. I. du Pont de Nemours and Company), bronze, carbon graphite, carbon steel, ceramic Al2O3, a perfluoroelastomer compound, such as CHEMRAZ™ marketed by Greene, Tweed, epoxy, HOSTELRY C™ alloy (marketed by Haynes International, Inc.), KALES™ elastomer (marketed by DuPont Performance Elastomers), polychlorotrifluoroethylene, NYLON™ (marketed by E. I. du Pont de Nemours and Company), Polyetherether Ketone (PEEK), polyphenylene sulfide, and PTFE.

The optical ion sensor 112 includes a film including a suspension of optical ion sensor matrices. The optical ion sensor matrices, in general, include an ionophore, an additive, and a chromionophore suspended in a polymer phase, for example, of polyvinyl chloride (PVC). The polymer phase also includes a plasticizer such as DOS. An ionophore substance that allows targeted ions to move across or into a membrane. Preferably the ionophore is selected to be lipid soluble. In addition, the ionophore is preferably an electrically neutral compound that forms a complex with a target ion. The ionophore is optically inactive in the visible spectrum and does not change absorbance or fluorescence depending on its state of complexation.

A chromoionophore is an ionophore that changes its optical properties in the visible spectrum depending on the state of complexation. Chromoionophores are preferably proton sensitive dyes that change absorbance (and fluorescence in many cases) depending on its degree of hydrogen complexation (protonation). The chromionophores are preferably highly lipophilic to prevent the chromionophores from leaching out of the optical ion sensor matrix. Suitable chromoionophores include Chromoionophore II and Chromoionophore III. Chromoionophore II exhibits light absorbance peaks at 520 nm and 660 nm and a fluorescent emission peak at 660 nm. Chromoionophore III has light absorbance peaks at 500 nm and 650 nm and fluorescent emission peaks at 570 nm and 670 nm.

For optical ion sensors targeting cations, the additive can be any inert lipophilic component that has a negative charge associated with it. For optical ion sensors targeting anions, the additive is positively charged. The purpose of the additive is to imbed charge sites within the polymer phase, to help enforce charge neutrality within the optical ion sensor 112. The additive allows the polymer phase to carry an equal amount of charged particles as additive. The concentration ratio of additive to chromoionophore is preferably 1:1, thereby allowing the chromoionphore to become completely protonated or de-protonated. One suitable additive for optical ion sensors targeting negative ions is potassium Tetrakis[3,5-bis(trifluoromethyl)phenyl]borate (KTFPB). The lipophilic anionic component TFPB-molecules are retained by the polymer phase and the potassium ions are either complexed by the ionophore, or expelled into the sample solution through diffusion. In one particular implementation, the optical ion sensor film is composed of a suspension produced from about 60 mg of DOS, 30 mg of PVC, and up to about 5 mg, of additive, ionophore, and chromionophore.

Once the above components are dissolved into the polymer phase to form the optical ion sensor 112 and are exposed to a sample solution, the optical ion sensor 112 becomes active. It now continuously extracts or expels analyte cations (system can work with anions as well using ion coextraction) depending on ion activity in the sample solution. With a 1:1 additive-chromoionophore ratio, with zero target ions present in the sample solution, the optical ion sensor 112 remains completely protonated to achieve charge neutrality. As the target ion concentration increases, the ionophores in the optical ion sensor 112 extract the target ions into the optical ion sensor 112. To maintain charge neutrality of the optical ion sensor 112, hydrogen ions are stripped from the chromoionphores in the optical ion sensor 112 and expelled into the sample solution. The expelling of hydrogen ions alters the pH of the optical ion sensor 112, thereby altering its fluorescent properties. To detect analyte anions (for example, chloride or nitrite ions), the optical ion sensor uses ion-coextraction, as opposed to proton expulsion. To detect neutral analytes, an additional agent known to interact with the target analyte to yield an ion is added to the biological sample holder 104. An ionophore is then selected to detect the resultant ion.

The following is a non-limiting, illustrative list of target ion/ionophore pairings suitable for use in the optical ion sensors: Potassium/Potassium Ionophore III (BME-44), Sodium/Sodium Ionophore IV, Sodium/Sodium Ionophore V, Sodium/Sodium Ionophore VI, Calcium/Calcium Ionophore III, and Calcium/Calcium ionophore IV. For target anions, illustrative target ion/ionophore pairings include chloride/Chloride Ionophore III and nitrite/Nitrite Ionophore I.

The film of the optical ion sensor can be produced in various ways. In one implementation, as described above, a predetermined amount of the optical ion sensor suspension (i.e., the combined polymer phase, ionophore, additive, and chromionophore) is dissolved in a solvent, such as THF. The solution is then deposited, sprayed, or spun onto a surface. The solvent then evaporates leaving the optical ion sensor film on the surface.

In another implementation, the film is formed form a deposition of optical ion sensor microspheres. To produce the microspheres, an optical ion sensor emulsion is formed by injecting an optical ion sensor suspension dissolved in THF (e.g., 16 mL THF/100 mg PVC) into a pH buffered solution. The optical ion sensor suspension includes approximately 60 mg of DOS, 30 mg of PVC, and up to approximately 5 mg of chromionophore, additive, and ionophore. The emulsion is then submerged in a sonicating water bath. Typically, 50 µL of the optical ion sensor suspension/THF solution is injected into 1,000-1,500 µL of buffered solution. The resulting emulsion contains a mixture of spherical optical ion sensor particles ranging in size from 200 nanometers to 20 microns. The resulting emulsion can be spun, sprayed, or evaporated onto any surface to create a porous optical ion sensor membrane. Films formed from microspheres tend to expose a greater surface area of optical ion sensor to a given sample, yielding improved performance characteristics.

The optical ion sensor support 102 also supports a pair of electrodes 117, which are coupled to opposite sides of the support 102. The electrodes 117 are also preferably THF resistant and can be made of, for example, and without limitation, platinum or silver chloride. Alternative electrode configurations are described below in relation to FIGS. 3 A-D.

The optical ion sensor support 102 includes an agent introduction means 118. The agent introduction means 118 can include a channel bored through the post 114, a pipette, or an electro-mechanical dispenser device, such as a solenoid or electrostatically driven plunger or syringe. The pipette or electro-mechanical dispenser may be positioned within a borehole formed in the post 114, or it may be coupled to the platform 116. The agent introduction means 118 allows a user to introduce an agent into the biological sample holder 104. In alternative implementations, the agent introductions means 118 can be attached to the platform 116. The agent introduction means 118 may be coupled to an agent reservoir 120 which stores the agent to be introduced. In alternative implementations, the optical ion sensor support 102 includes two or more agent introduction means 118. In one such implementation, a first agent introduction means 118 is used to introduce a therapeutic or other biologic into the biological sample holder to assay its effect on the cells located therein. The additional agent introduction means 118 may be used for introducing other therapeutics or biologics or to introduce optical ion sensor particles, described further below, for uptake, for example, into the cells in the biological sample holder 104.

The electrodes 117 coupled to the optical ion sensor support 102 are energized by a voltage source 122. The voltage source 122 may provide an AC and/or DC voltage to the electrodes 117 for generating an electric field between the electrodes 117. The voltage source 122, in one implementation is capable of providing a sufficient voltage to electroporate cells 124 in the biological sample holder. The voltage source 122 can also provide generate smaller magnitude voltages that are sufficient to activate voltage-gated ion channels in the cells 124, but not to cause electroporation.

The biological sample holder 104 holds a biological sample for analysis by the cell assay system 100. The biological sample can include, as illustrated in FIG. 1, cells 124 adhered to the walls of the biological sample holder 104, for example, in a monolayer, or cells 124 suspended in a liquid buffer. The biological sample holder 104 is preferably transparent, or at least includes a transparent region through which the optical ion sensor 112 can be excited and through which the results of such excitement can be monitored.

The optical ion sensor 112 is illuminated with a light source 106 to excite the chromionophores suspended therein. The light source preferably can be tuned to generate one or more predetermined wavelengths of light, preferably in the visible portion of the electromagnetic spectrum, selected to excite the particular chromionophore used in the optical ion sensor 112. Alternatively, the light source may generate a wide spectrum light. In one implementation, the light source 106 is coupled to the optical ion sensor support 102.

The fluorescence of the optical ion sensor 112 is detected by a light sensor 108. The light sensor 108 may include a charge coupled device, a fluorometer, a photomultiplier tube, or other suitable device for measuring fluorescence. In one implementation, a spectrophotofluorometer is used to satisfy the roles of the light source 106 and the light sensor 108. The light sensor 108 may also be coupled to the optical ion sensor support 102.

A robotics assembly 110 controls the position of the optical ion sensor support 102 and/or the biological sample holder 104 to control the introduction of the optical ion sensor 112 into the biological sample holder. In the illustrative embodiment, the robotics assembly 110 includes a robotic arm 124 coupled to the platform 116 of the optical ion sensor support 102 for raising and lowering the optical ion sensor support 102 into and out of the biological sample holder. The robotic arm 124 may also provide three dimensional movement control of the optical ion sensor support 102, for example, to move the optical ion sensor support 102 between different biological sample holders 104, for example, arranged as multiple wells in a standard multi-well plate. The robotics assembly may also move the optical ion sensor support 102 between a biological holder sample 104 and a preparation bath used to protonate the optical ion sensor film 112 and to strip the optical ion sensor 112 of target ions previously brought into the optical ion sensor 112.

The computing device 111 controls the various components of the cell assay system 100. The computing device 111 may be a single computing device or multiple computing devices providing the various functionalities used to control the cell assay system. These functionalities are provided by an excitation control module 126, a voltage control module 128, an agent introduction module 130, a robotics module 132, and an analysis module 134. The excitation control module 126 controls the light source 108 to emit one or wavelengths of excitation light. The voltage control module 128 controls the voltage source 122 to generate a constant or time-varying electric field between the electrodes 117. The agent introduction module 130 controls the introduction of an agent into the biological sample holder 104 via the agent introduction means 118. The robotics module 134 controls the robotics assembly 110. The analysis module 134 analyzes the output of the light sensor 108. For example, the analysis module 134 may compare the output of the light sensor 108 to determine the response of applying various voltages across the electrodes 117. The analysis module may also analyze the output of the light sensor 108 before and after an agent is introduced into the biological sample holder 104 to determine the effect of the agent on the cells 124 in the biological sample holder 104. The analysis module 134 may also control the other modules in the computing device, i.e., the excitation control module 126, the voltage control module 128, the agent introduction module 130, and the robotics module 132, to coordinate an assay protocol. The computing device 111 and/or devices may also include various user interface components, such as a keyboard, mouse, trackball, printer, and display.

A module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module. A module of executable code could be a single instruction, or many instructions, and may even be distributed over several different code segments, among different programs, and across several memory devices.

The various modules are in communication with the various devices they control or obtain data from. They maybe connected over a local area network, wirelessly, over a bus, or over typical cables known in the art of computer interfaces for connecting computing devices with peripherals.

Figure 2A:
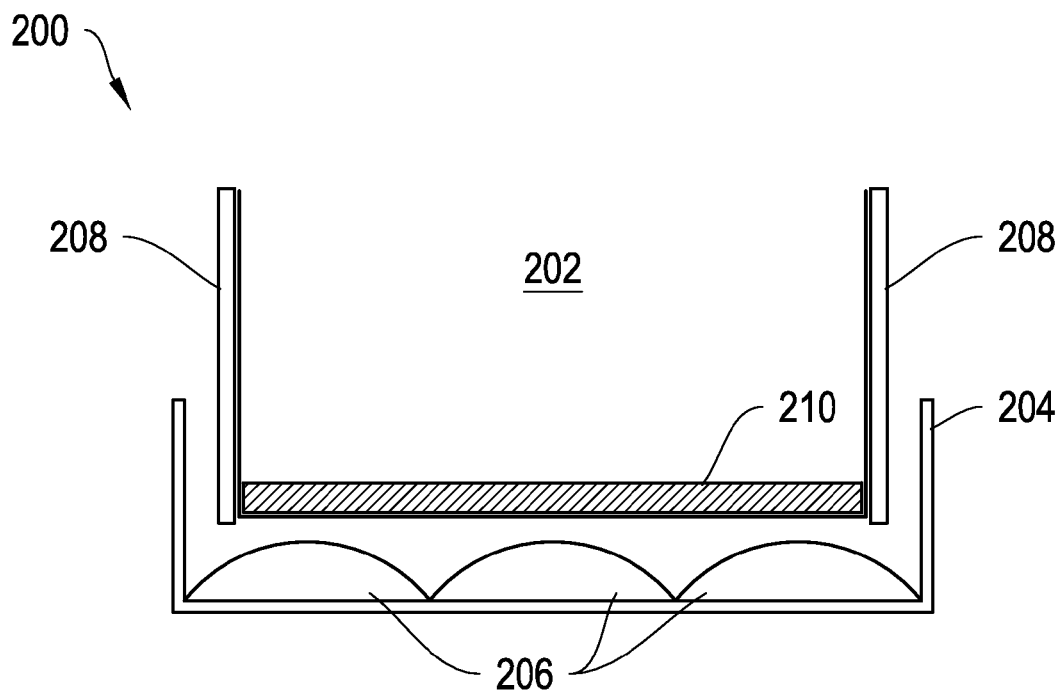
FIGS. 2A-2D are cross sections of various optical ion sensor arrangements suitable for use in various implementations of the cell assay system of FIG. 1, according to an illustrative embodiment of the invention.

FIGS. 2A-2D are cross sections of various optical ion sensor arrangements suitable for use in various implementations of the cell assay system 100 of FIG. 1. FIG. 2A is a cross section of a first optical ion sensor arrangement 200 suitable for use in the cell assay system of FIG. 1. The optical ion sensor arrangement 200 includes an optical ion sensor support 202 and a biological sample holder 204. The biological sample holder 204 includes a monolayer of cells 206 adhered to the biological sample holder 204. Alternatively, the biological sample holder 204 holds cells suspended in a buffer. The optical ion sensor support 202 and biological sample holder 204 correspond to the optical ion sensor support 102 and biological sample holder 104 of FIG. 1. Electrodes 208 are coupled to opposing sides of the optical ion sensor support 202. A optical ion sensor film 210 is coupled to the distal end of the optical ion sensor support 202.

Figure 2B:
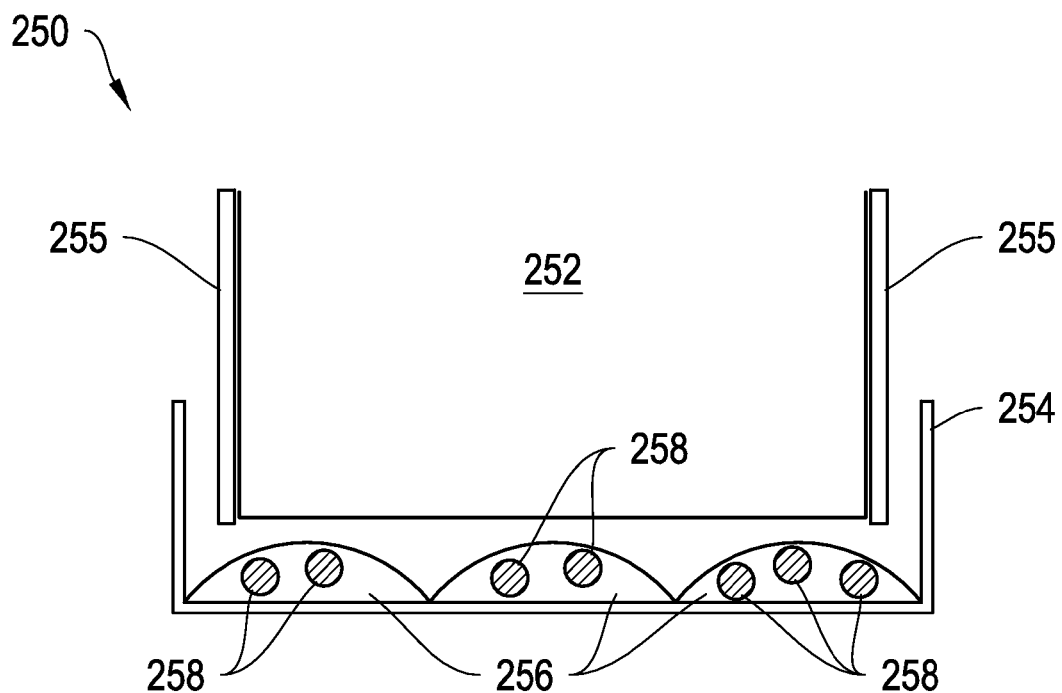

FIG. 2B is an alternative optical ion sensor arrangement 250 for use in an alternative implementation of the cell assay system 100 of FIG. 1. The optical ion sensor arrangement 250 includes an electrode support 252 and a biological sample holder 254. Electrodes 255 are coupled to opposing sides of the electrode support 252. The biological sample holder 254 includes a monolayer of cells 256 adhered to the surfaces of the biological sample holder 254 or cells suspended in a buffer. Instead of including an optical ion sensor film adhered to a support, the optical ion sensor arrangement 250 relies upon optical ion sensor particles 258 introduced into the cells 256 adhered to the biological sample holder 254.

To introduce optical ion sensors into cells, the optical ion sensors are produced as optical ion sensor particles 258. The optical ion sensor particles 258 are fabricated in a similar fashion as the optical ion sensor film 112 described above. One such particle 258, the optical ion sensor nanosphere, is produced according to the following procedure. First a optical ion sensor suspension is dissolved in 500 µl of THF. The suspension preferably includes 60 mg of DOS, 30 mg of PVC and up to about 5 mg of chromoionophore, ionophore, and additive to form an optode solution. Then, 500 µl of $CH_2Cl_2$ is added to bring the total volume to 1 ml. Next, a PEG-lipid solution is prepared by adding dissolving a PEG-lipid into 5 ml of a water, salt and buffer solution. A TAT peptide can be added to the PEG-lipid via an amine linkage to aid the resulting nanospheres in entering cells.

The nanospheres are formed by adding 100 µl of optode solution drop wise to 5 ml of the PEG-lipid solution while the solution is being sonicated by a probe tip sonicator. Additional sonication is performed for approximately 2-3 minutes. The resultant nanosphere solution is sprayed through a nitrogen feed air gun into a beaker several times to remove excess solvent. If desired, the nanosphere solution is pushed through a 0.22 µm filter to remove the larger spheres.

The optical ion sensor particles 258 are introduced into the cells 256 in one of two ways. In one method, the optical ion sensor particles 258 are introduced into a buffer liquid deposited in the biological sample holder 254. A voltage source then generates a voltage across the electrodes 255 sufficiently strong to electroporate the cells 256, thereby allowing the optical ion sensor particles 258 to enter directly into the cells. In the other method, the surfaces of the optical ion sensor particles 258 are first coated with a substance, for example transferrin or folate, which aid in the optical ion sensor particles 258 crossing over cell membranes. The optical ion sensor particles 258 are introduced into a buffer in the biological sample holder 254. The cells 256 bring the optical ion sensor particles 258 into their interior in vesicles via endocytosis, pinocytosis, or phagocytosis, or similar biological processes. The substance applied to the optical ion sensor particles 258 breaks down the vesicle membrane, releasing the optical ion sensor particles 258 into the cell cytoplasm.

Figure 2C:
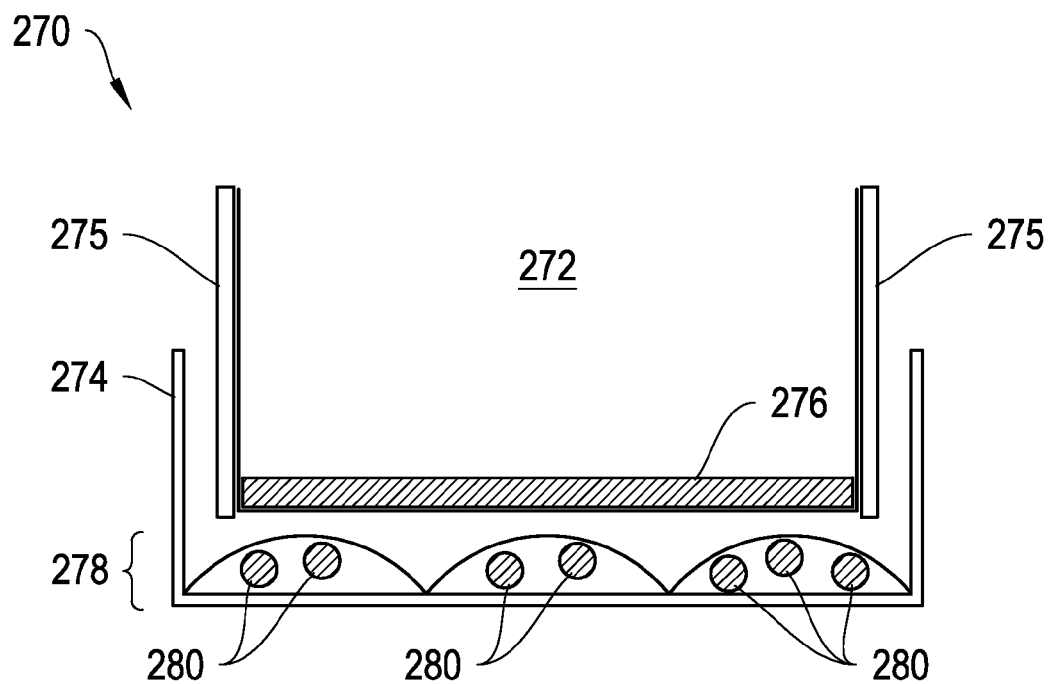

FIG. 2C is a second alternative optical ion sensor arrangement 270 for use in an alternative implementation of the cell assay system 100 of FIG. 1. The optical ion sensor arrangement 270 includes an optical ion sensor support 272 and a biological sample holder 274. Electrodes 275 are coupled to opposing sides of the optical ion sensor support 272. An optical ion sensor film 276 is coupled to the distal end of the optical ion sensor support 272. A cell monolayer 278 adheres to the surfaces of the biological sample holder 274. Alternatively, cells are suspended in a buffer. In addition, optical ion sensor particles 280 are introduced into the cells of the cell monolayer 278. Preferably the chromionophores used in the optical ion sensor film 276 differ from the chromionophores used in the optical ion sensor particles 280. In particular, the different chromionophores preferably have distinguishable fluorescence characteristics such that an analysis module analyzing the output of a light sensor monitoring the optical ion sensor arrangement 270 can differentiate between the output of the optical ion sensor film 272 and the optical ion sensor particles 280. As a result, the analysis module can differentiate between intracellular target ion concentration and extracellular target ion concentration. In addition, the optical ion sensor film 272 may include different ionophores than those included in the optical ion sensor particles 280. Thus, the optical ion sensor arrangement 270 can monitor the concentrations of two different target ions.

Figure 2D:
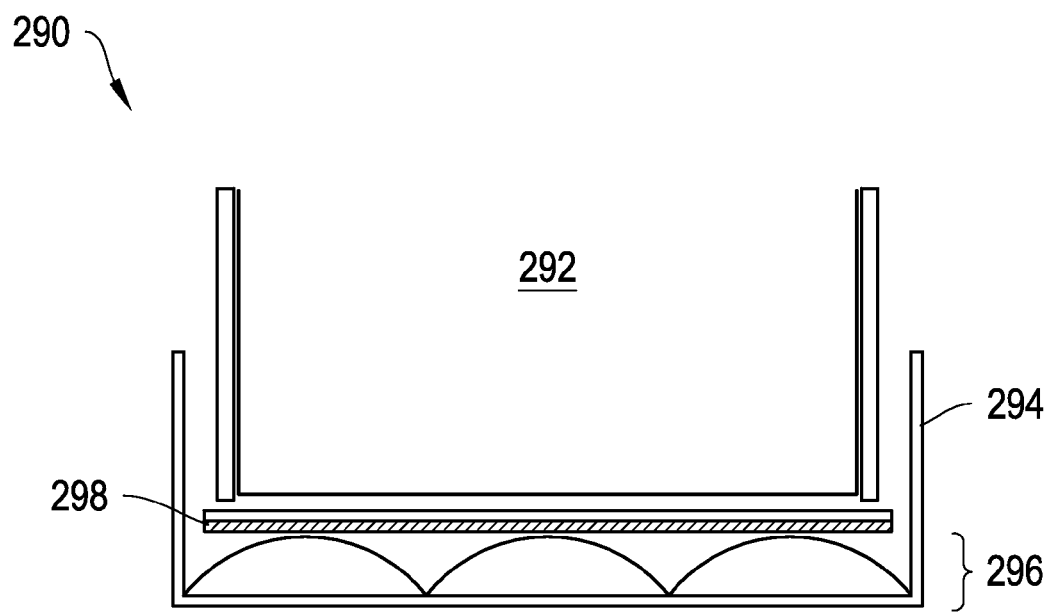

FIG. 2D is a third alternative optical ion sensor arrangement 290 for use in an alternative implementation of the cell assay system 100 of FIG. 1. The optical ion sensor arrangement 290 includes an electrode support 292 and a biological sample holder 294. The biological sample holder 294, in addition to a cell monolayer 296 or cells suspended in a buffer, includes a removable optical ion sensor film 298. The removable optical ion sensor film 298, for example, can be a glass cover slip or other transparent surface coated with an optical ion sensor film.

Figure 3A:
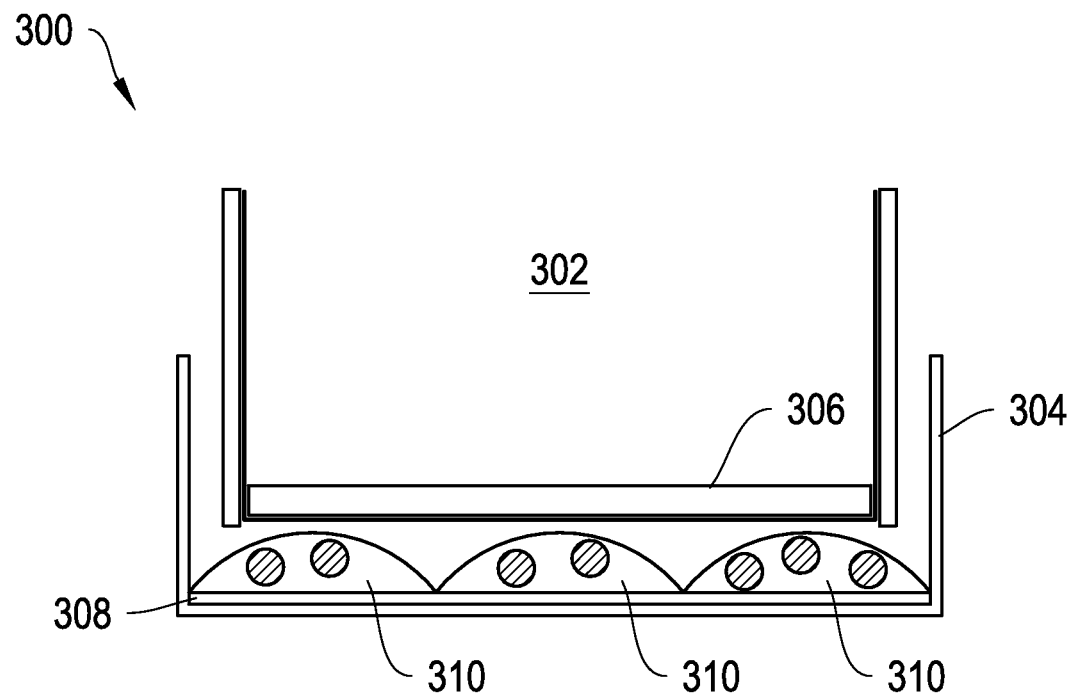
FIGS. 3A-3D illustrate alternative electrode arrangements suitable for various implementations of the cell assay system of FIG. 1, according to an illustrative embodiment of the invention.

FIGS. 3A-3D illustrate alternative electrode arrangements suitable for various implementations of the cell assay system 100 of FIG. 1. FIG. 3A is a cross section of a first alternative electrode arrangement 300. The electrode arrangement 300 includes an electrode support 302 and a biological sample holder 304. The electrode support 302 includes a first electrode 306 coupled to the distal end of the electrode support. A second electrode 308 is coupled to the bottom of the biological sample holder 304. The second electrode 308 is preferably formed from a transparent conductor, such as indium tin oxide. The biological sample holder 304 includes a monolayer of cells 310 adhered to the surface of the second electrode 308. Alternatively, the cells 310 may be suspended in a fluid in the biological sample holder 310.

Figure 3B:
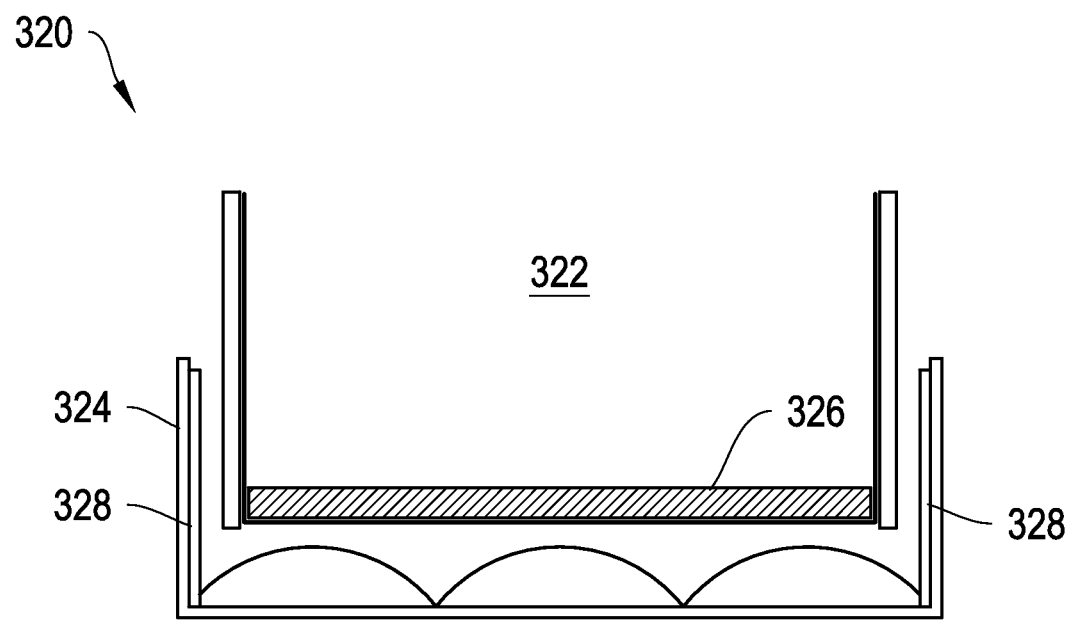

FIG. 3B is a cross section of a second alternative electrode arrangement 320, according to an illustrative embodiment of the invention. The electrode arrangement 320 includes and optical ion sensor support 322 and a biological sample holder 324. The optical ion sensor support 322 includes an optical ion sensor film 326 coupled to its distal end. Electrodes 328 are coupled to opposing sides of the biological sample holder 324.

Figure 3C:
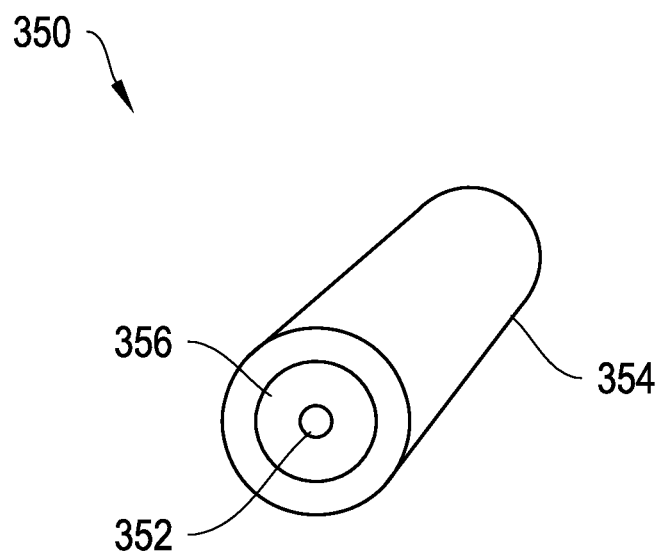

FIG. 3C is perspective view of a third alternative electrode arrangement 350, according to an illustrative embodiment of the invention. In the third electrode arrangement 350, electrodes 352 and 354 are arranged coaxially, with one electrode 352 filling a cavity in the interior of an electrode support 356, which can be positioned in a biological sample holder. The second electrode 354 surrounds the exterior of the electrode support 356.

Figure 3D:
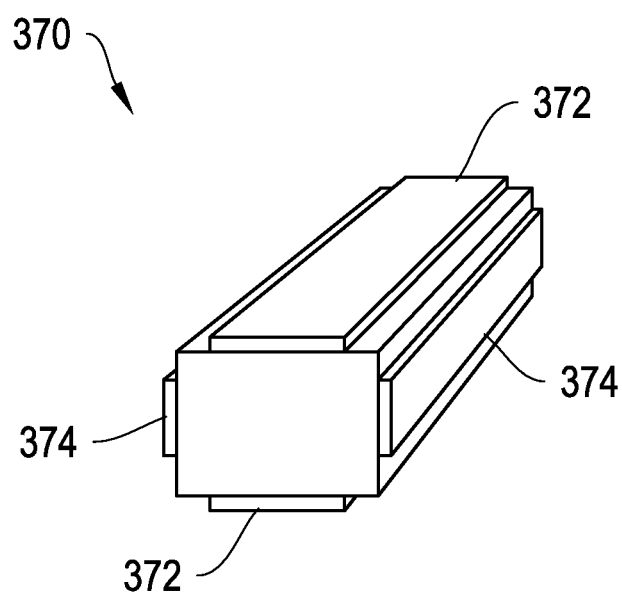

FIG. 3D is perspective view of a fourth alternative electrode arrangement 370, according to an illustrative embodiment of the invention. This electrode arrangement 370 includes two pairs of electrodes 372 and 374 coupled to an optical ion sensor film 376. Each pair of electrodes 372 and 374 can be individually energized to generate perpendicular electrical fields across cells in a biological sample holder.

Figure 4A:
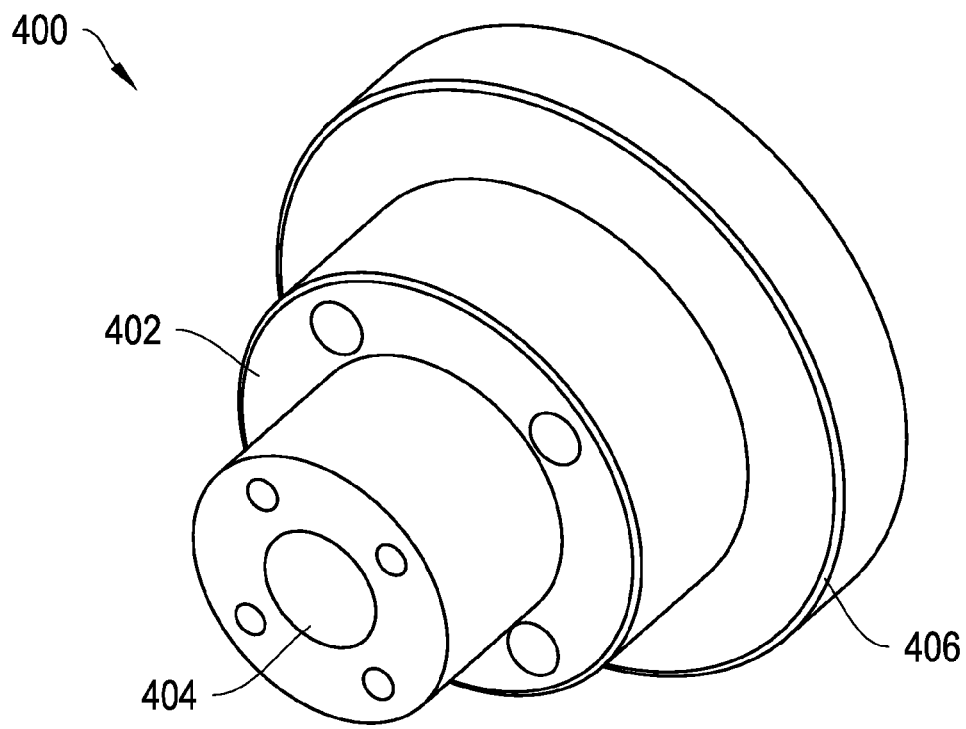
FIG. 4A is a perspective view of an illustrative optical ion sensor support, suitable for use in the cell assay system of FIG. 1, according to an illustrative embodiment of the invention.

FIG. 4A is a perspective view of an illustrative optical ion sensor support 400, suitable for use in the cell assay system 100 of FIG. 1. The optical ion sensor support 400 includes three constituent components, a housing 402, an optical ion sensor insert 404, and a platform 406, described in further detail in FIGS. 4B-4D.

Figure 4B:
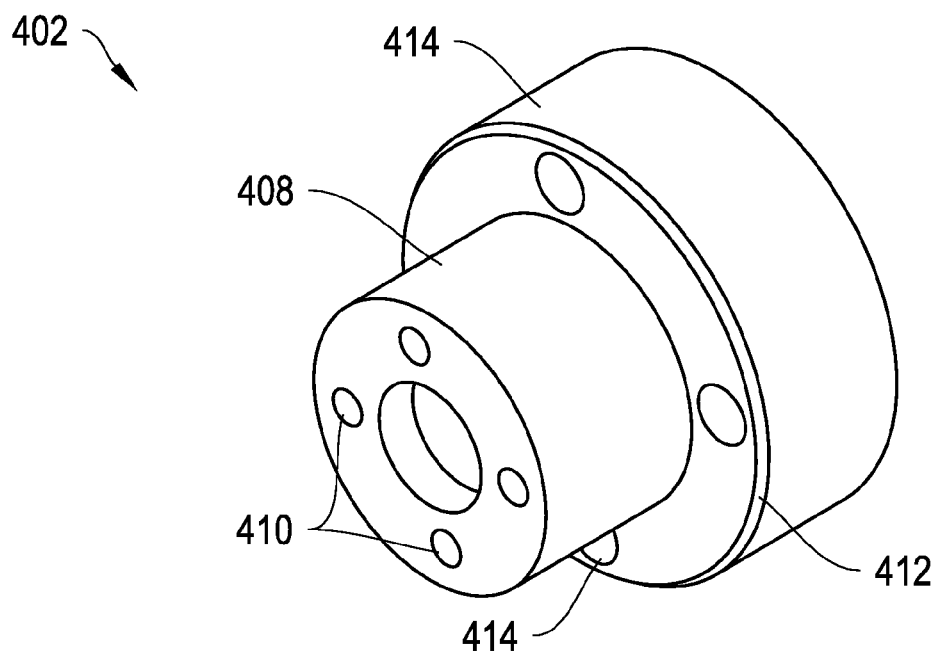
FIGS. 4B-4D are perspective views of components of the optical ion sensor support of FIG. 4A, according to an illustrative embodiment of the invention.

FIG. 4B is a perspective view of the housing 402 of the optical ion sensor support 400. The housing 402 includes a post 408 sized for insertion into a biological sample holder. Electrodes 410 are formed in the post. In one implementation, the distance between the platform 406 and the housing 402 can be changed to adjust the distance between cells in a biological sample holder and the distal end of the optical ion sensor insert 404. The housing 402 includes two dosing holes 412 for introducing agents into a biological sample holder. The housing 402 also includes an pair of mounting holes 414 for coupling the housing 402 to the platform 406, and, in some implementations, through the platform 406 to a robotic arm. The mounting holes 414 may be threaded, for example, for acceptance of bolts to couple the components together. Adjustment of such bolts, in one implementation can be used to adjust the distance of the distal end of the optical ion sensor insert 404 to cells in a biological sample holder.

Figure 4C:
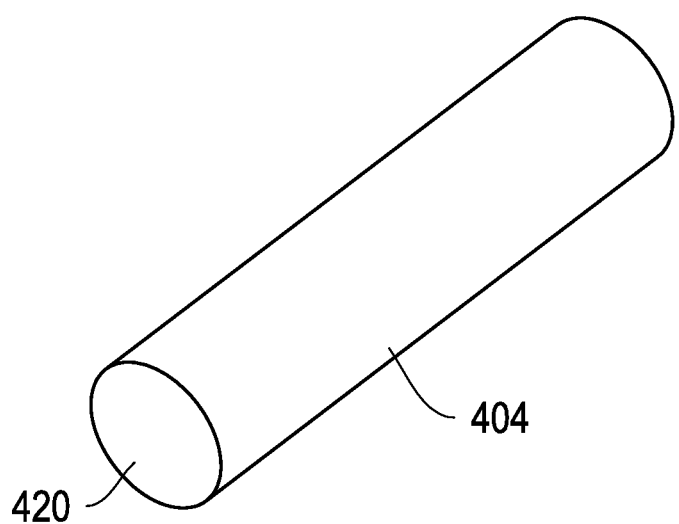

FIG. 4C is a perspective view of the optical ion sensor insert 404, according to an illustrative embodiment of the invention. The optical ion sensor insert 404 is constructed of DERLIN™ Acetal polymer and is shaped to fill a cavity milled into the housing 402. The optical ion sensor insert 404 can be removably inserted into the housing 402 such that it its distal end aligns with the bottom surface of the housing 402. A optical ion sensor film 420 is coupled to the distal end of the optical ion sensor insert 404. During operation, various optical ion sensor inserts 404 incorporating different ionophores in their optical ion sensor films 420 can be alternately inserted and removed into the housing 402 to measure the varying concentrations of corresponding ions.

Figure 4D:
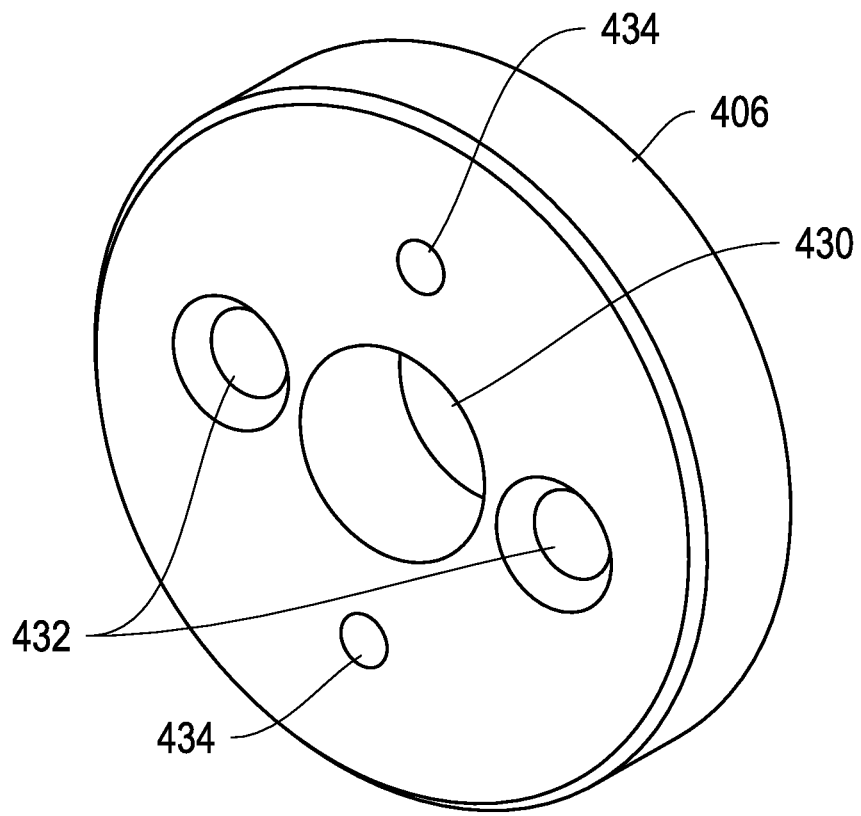

FIG. 4D is a perspective view of the platform 406 used in the optical ion sensor support 400. The platform includes a cavity 430 through which the optical ion sensor insert 404 can be inserted and withdrawn, along with dosing holes 432 and mounting holes 434 which align with the dosing holes 412 and mounting holes 414 of the housing 402.

Figure 5:
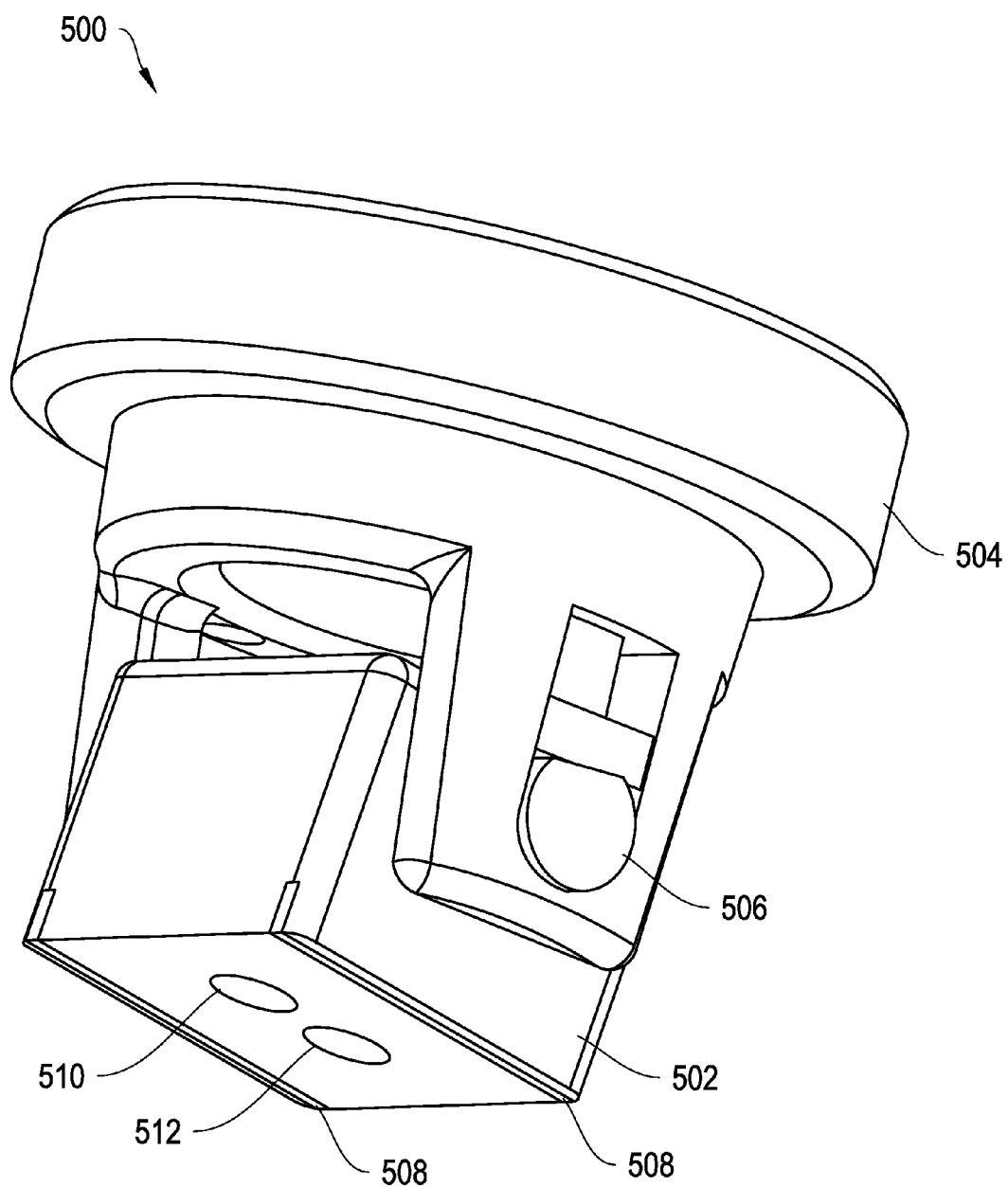
FIG. 5 is perspective view of an alternative optical ion sensor support suitable for use in the cell assay system of FIG. 1, according to an illustrative embodiment of the invention.

FIG. 5 is perspective view of an alternative optical ion sensor support 500 suitable for use in the cell assay system 100 of FIG. 1. The optical ion sensor support 500 includes a body 502 and a platform 504 coupled together at a hinge 506. The body 502 includes two electrodes 508 and two optical ion sensor films 510 and 512. The optical ion sensor films 510 and 512 may include ionophores that are selective for the same ion. Alternatively, the optical ion sensor films 510 and 512 include ionophores that are selective for different ions. In such embodiments, the optical ion sensor films 510 and 512 also include different chromionophores whose fluorescence characteristics can be distinguished from one another. In one embodiment the hinge 506 keeps the body 502 at an angle with respect to the horizontal to reduce the likelihood of bubble formation at the site of the electrodes 508. In other embodiments, the optical ion sensor films 510 and 512 are disposed on the distal ends of removal optical ion sensor inserts, such as the optical ion sensor inserts 404 of FIG. 4A. The hinge 506, in this embodiment, allows the body 502 to rotate with respect to the platform 504 such that the optical ion sensor inserts are accessible for insertion and removal.

Figure 6:
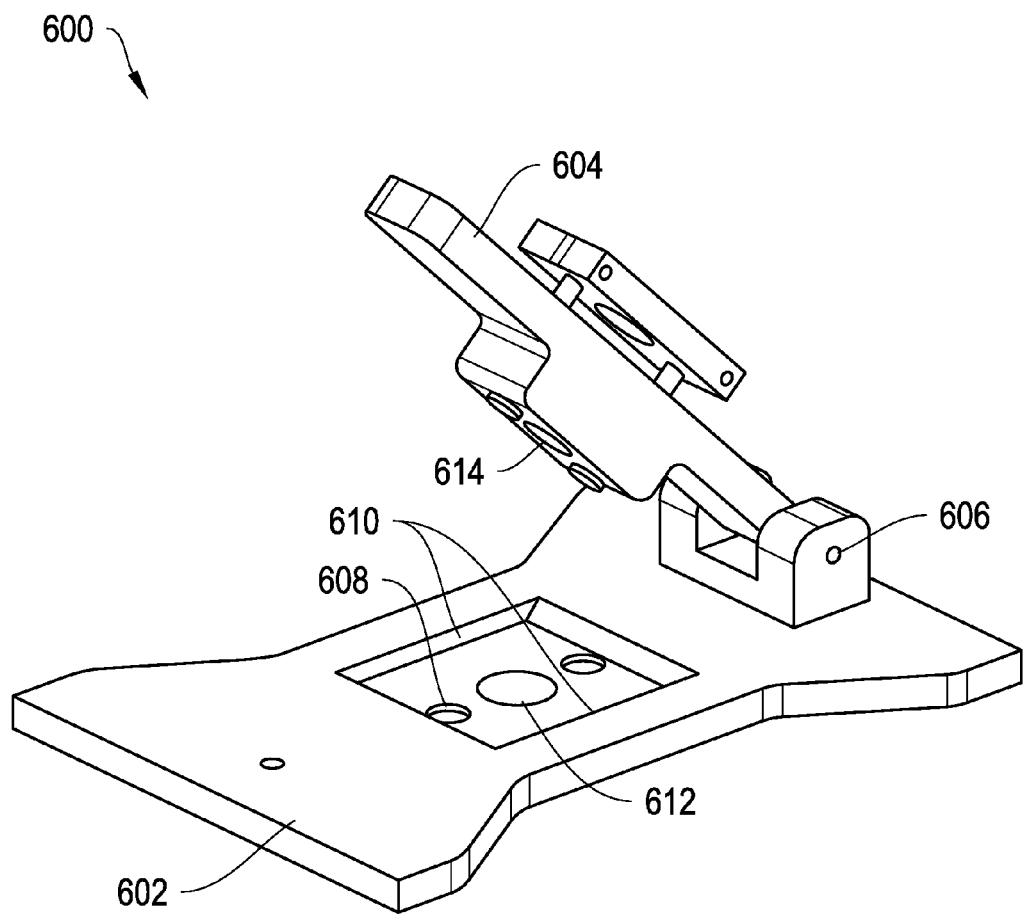
FIG. 6 is a perspective view of a optical ion sensor support/biological sample holder configuration suitable for use on a microscope stage, according to an illustrative embodiment of the invention.

FIG. 6 is a perspective view of a optical ion sensor support/biological sample holder configuration 600 suitable for use on a microscope stage. This configuration includes a base plate 602 coupled to a biological sample holder 604 at a hinge 606. The base plate 602 includes a bath 608. Electrodes 610 are coupled to at least two of the four opposing walls of the bath. A optical ion sensor film 612 is disposed in the bottom of the bath 608, for example, on a glass cover slip. The biological sample holder 604 includes a clamp to accept a transparent substrate with a cell monolayer formed thereon. The biological sample holder includes an optical through hole 614 allowing the fluorescence of the optical ion sensor film 612 to be viewed through the top of the biological sample holder 604 or through the bottom of the base plate 602. In one mode of operation, the base plate 602 is placed on the stage of a microscope. An optical ion sensor film 612 selective for a desired ion is placed within the bath 608, and the biological sample holder 604, holding a sample, is lowered into position. The resulting fluorescence can be monitored through the optical through hole 612 by a viewer via the microscope. Alternatively, a camera can be attached to the microscope to record the resultant fluorescence.

Figure 7:
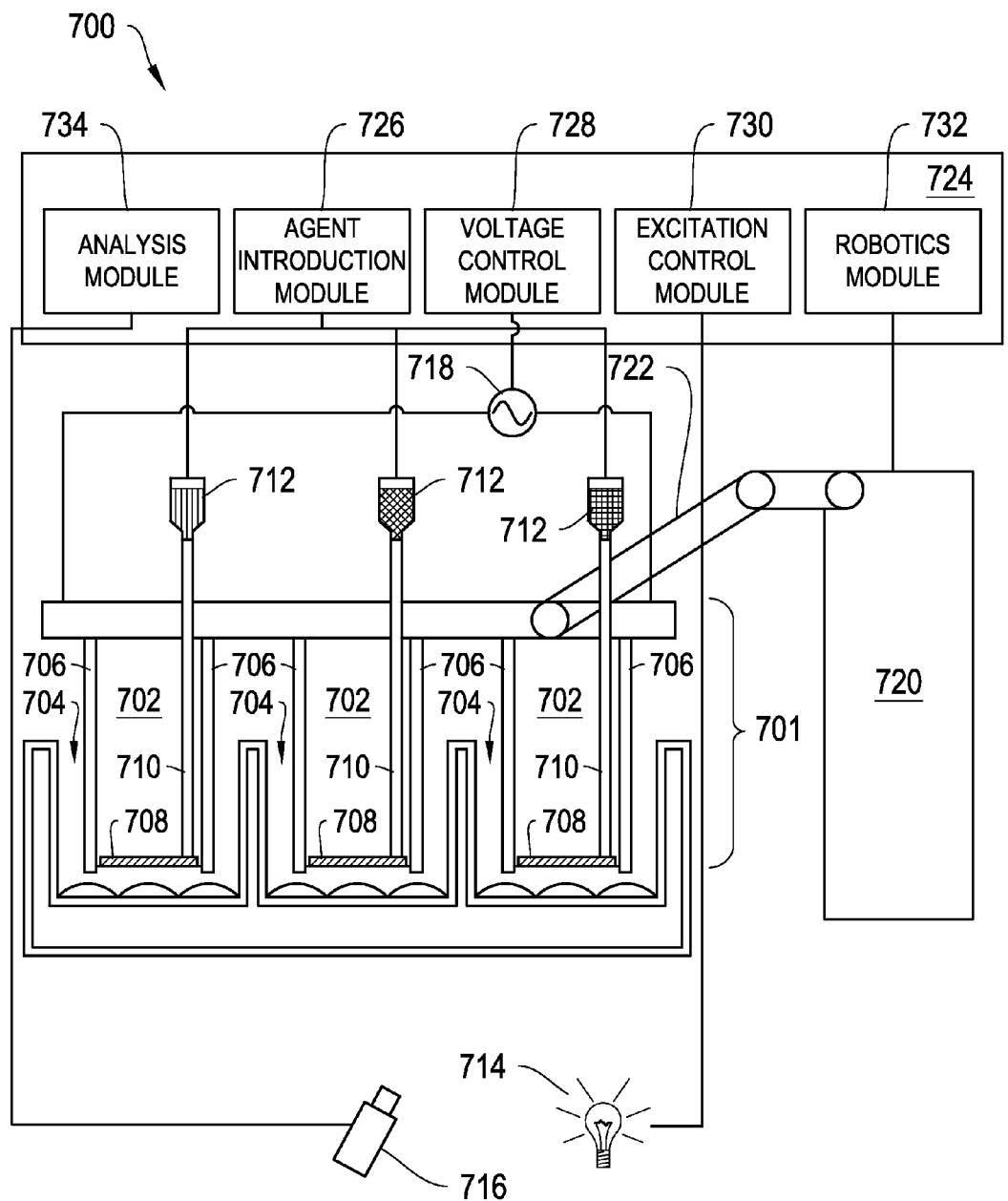
FIG. 7 is a schematic diagram of an alternative cell assay system, according to an illustrative embodiment of the invention.

FIG. 7 is a schematic diagram of an alternative cell assay system 700. The cell assay system 700 is similar to the cell assay system 100 of FIG. 1. However, the cell assay system 700 includes an array 701 of optical ion sensor supports 702. The optical ion supports 702 are sized and spaced in the array 701 such that the optical ion sensor supports 702 can be simultaneously introduced into multiple corresponding biological sample holders 704. The optical ion sensor supports 702 protrude from a platform 703. The array may be one-dimensional or two dimensional. The biological sample holders 704, in various implementations, are wells in a standard 6-, 12-, 24-, 48-, 96-, 384-, or 1534-well plate. The array 701 may include a sufficient number of optical ion sensor supports 702 to analyze an entire plate at once, or it may include a smaller number of optical ion sensor supports 702, requiring the array 701 be repositioned one or more times for each plate of biological sample holders 704 provided for analysis. Each optical ion sensor support 702 includes a corresponding set of electrodes 706, an optical ion sensor 708, and an agent introduction means 710. The electrodes can take the form of any of the electrode arrangements described above in FIG. 1, FIGS. 3A-3D, FIG. 4, FIG. 5, and FIG. 6.

The optical ions sensor 708 for each optical ion sensor support 702 can be arranged according to any of the optical ion sensor arrangements described above in FIG. 1, FIGS. 2A-2D, FIG. 4, FIG. 5, and FIG. 6. In one implementation, each optical ion sensor support 702 incorporates the same optical ion sensor 708. In alternative implementations, the optical ion sensor varies in each row or column of optical ion sensor supports 702 of the array 701. In still other implementations, the optical ion sensor 708 selected for each optical ion sensor support 702 is chosen individually or in a group-wise fashion.

The agent introduction means 710 corresponding to each optical ion sensor support 702, in one implementation, includes passive dosage holes for administering agents. In alternative implementations, the agent introduction means 710 includes a solenoid or electrostatically driven mechanisms for introducing agents into biological sample holders 704. In still another implementation, the agent introduction means 710 for each optical ion sensor support 702 includes a pipette. The agent introduction means 710 are preferably coupled to an agent reservoir 712. As depicted in FIG. 7, the agent included in each agent reservoir 712 may vary for each optical ion sensor support 702 or by row or column of optical ion sensor supports 702 in the array 701.

The cell assay system 700 includes at least one light source 714 for exciting the optical ion sensors 708 associated with each optical ion sensor support 702. In an alternative implementation, for example, each row of optical ion sensor supports 702 includes a different optical ion sensor 708. In this embodiment, the cell assay system 700 includes a separate light source 714 for each row tuned to the wavelength of the optical ion sensors 708 in that row. Alternatively, the cell assay system 700 may have separate light sources 714 for each optical ion sensor 708 or group of optical ion sensors 708.

Similarly, the cell assay system includes at least one light sensor 716. As with the light sources 714, the cell assay system may have a single light sensor 716 for the entire array, one light sensor 716 per row or column of optical ion sensor supports 702, or one light sensor 716 for each individual optical ion sensor 708 or group of optical ion sensors 708.

The cell assay system includes a voltage source 718 for generating voltages across the sets of electrodes 706. The voltage source 718 can connect to electrical interconnects integrated into the platform 703 of the array 701. In addition, the voltage source 718 can itself be incorporated into the platform 703. The voltage source 718 can provide an AC and/or a DC voltage.

The cell assay system 700 also includes a robotics assembly 720. The robotics assembly 720 can control the position of the platform in three dimensions using a robotic arm 722. The robotics assembly 720 can also maneuver multi-well plates into and out of position beneath the array 701 so that the array 701 can be used in high throughput assays, analyzing samples in multiple plates in series.

The various components described above are controlled and monitored by a computing device 724 similar to the computing device 111 of FIG. 1. The computing device 724 includes an agent introduction module 726 for controlling the agent introduction means 710, a voltage control module 728 for controlling the voltage source 718, a excitation control module 730 for controlling the light source(s) 714 included in the cell assay system, a robotics module 732 for controlling the robotics assembly 720, and an analysis module 734 for directing assay protocols and analyzing the output of the light sensor(s) 716 included in the cell assay system 700. For example, the analysis module 734 determines the concentrations of ions in the biological sample holders 704 over time. The analysis module 734 also compares the data collected for each biological sample holder 704 for comparative analysis. The comparative analysis may take into account knowledge of the various agents introduced into each respective biological sample holder 704.

Figure 8A:
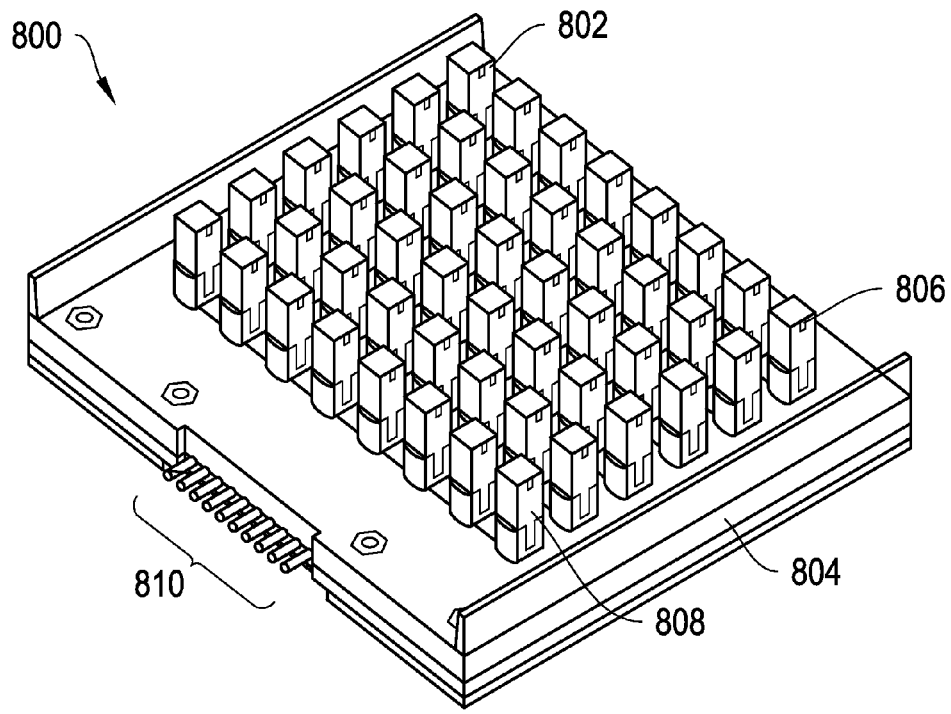
FIG. 8A is a perspective view of an optical ion sensor array suitable for use in the cell assay system of FIG. 7, according to an illustrative embodiment of the invention.

FIG. 8A is a perspective view of an optical ion sensor array 800 suitable for use as the array 701 in the cell assay system 700. The optical ion sensor array 800 includes 48 optical ion sensor support posts 802 protruding from a platform 804. Each optical ion sensor support post 802 is sized to fit into a well of a standard 48- or 96-well assay plate. The distal end of each ion support post 802 couples to an optical ion sensor 806. The optical ion sensors 806 coupled to the optical ion sensor support posts 802 may vary by row, by column, or by individual or group of optical ion sensor support posts 802. Silver chloride electrodes 808 couple to opposing sides of the optical ion sensor support posts 802. The electrodes 808 electrically connect to interconnects in the interior of the platform 804. The interconnects connect to a voltage source via a series of pins 810 extending from one side of the platform 804.

Figure 8B:
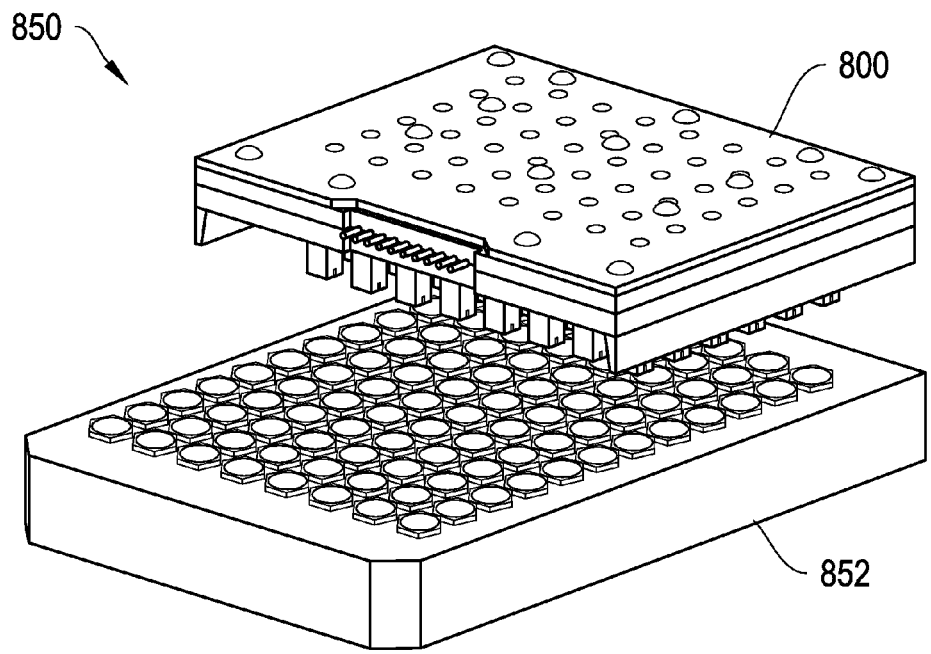
FIG. 8B is a perspective view of a optical ion sensor array and biological sample holder arrangement, according to an illustrative embodiment of the invention.

FIG. 8B is a perspective view of a optical ion sensor array/biological sample holder arrangement 850. The arrangement 850 includes the array 800 of FIG. 8A and a 96-well plate biological sample holder 852. In operation, the array 800 is lowered into a first half of the biological sample holder 852 for a first assay. It is then lowered into the second half of the biological sample holder 852 for a second assay.

Figure 9:
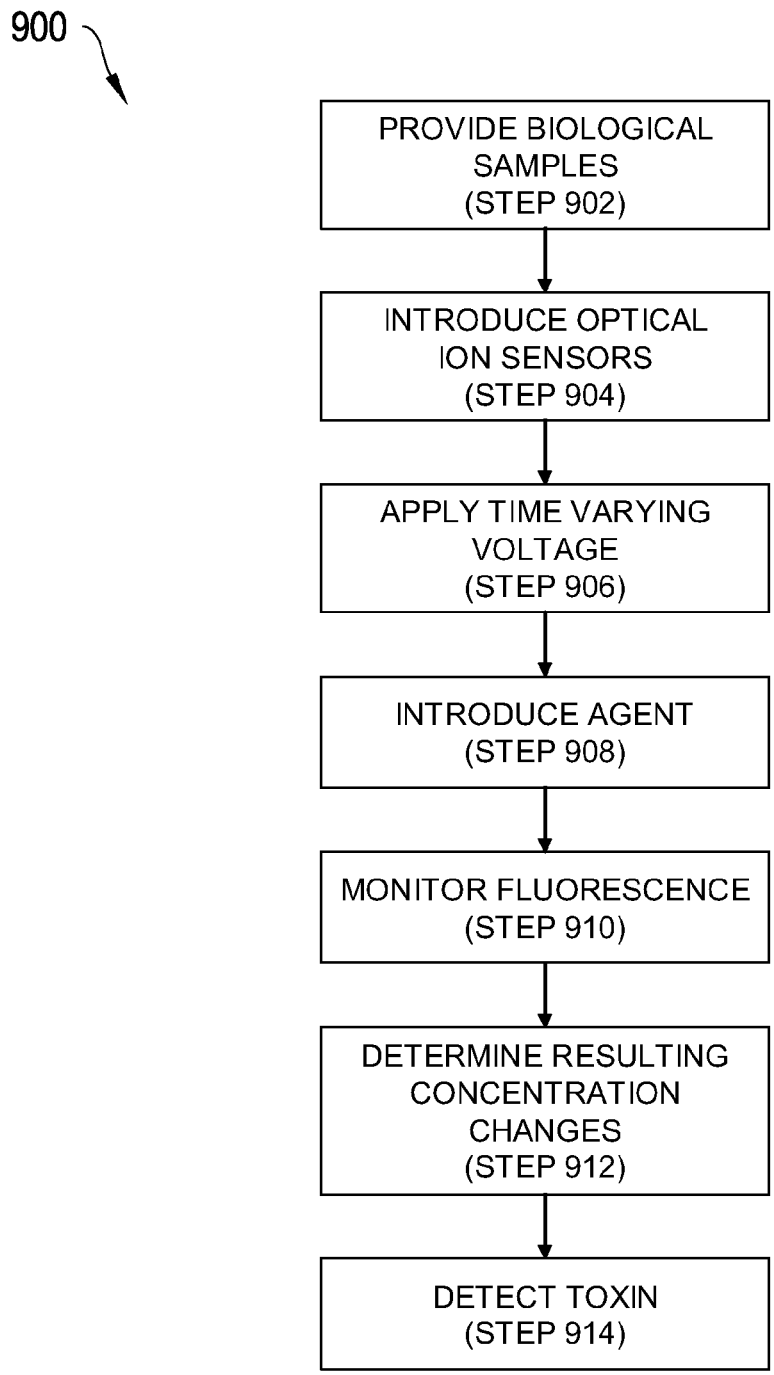
FIG. 9 is a flow chart of a method conducting a biological assay using a cell assay system, such as the cell assay system of FIG. 7, according to an illustrative embodiment of the invention.

FIG. 9 is a flow chart of a method conducting a biological assay 900 using a cell assay system, such as the cell assay system 700 of FIG. 7. The following methodology is particularly suited for analyzing the impact of various agents on cellular voltage-gated ion channels, including potassium channels, sodium channels, and calcium channels. The method begins with providing a plurality of biological sample holders holding biological samples (step 902). The biological samples, in one implementation include cells either adhered to the walls of the biological sample holders covered with a buffer solution, or cells suspended in a buffer solution. Though any type of cell can be monitored using the cell assay system, cells of particular interest include nerve cells or muscle cells in which voltage-gated ion channels regulate the propagation of action potentials along cell membranes and between cells. Other cells of interest include cells with non-wild-type ion channels, for example, cells with overactive or underactive voltage-gated ion channels.

Next, optical ion sensors are introduced into the biological sample holders (step 904). In one implementation, the optical ion sensors are introduced into the buffer surrounding the cells by lowering optical ion sensor support posts into the biological sample holders. In the alternative, or in addition, optical ion sensor particles are introduced into the cells in the biological sample holders. As described above, optical ion sensor particles can be introduced either by electroporating the cells via electrodes positioned in the biological sample holders or by the chemistry applied to the optical ion sensor particles breaching vesicle membranes within the cells. Similarly, the optical ion sensor sensors can be introduced into the cells using pico-injection, bead loading, a gene gun, or through liposomal delivery techniques known in the art. As described above the optical ion sensors include at least one ionophore for selectively binding a predetermined ion thereby altering a pH of a optical ion sensor and one pH-sensitive chromionophore for optically indicating the concentration of an ion in a fluid surrounding the optical ion sensor corresponding to the ionophore. Ion concentration is indicated by the pH of the optical ion sensor and the resulting fluorescence of the chromionophore.

Sets of electrodes then apply a time-varying voltage across the cells in the biological sample holders (step 906). Preferably at least one of the electrodes in each set is coupled to an optical ion sensor support post with which an optical ion sensor is introduced into a particular biological sample holder.

At step 908, an agent, such as a therapeutic, toxin, biological macromolecule (such as a nucleic acid, an antibody, a protein or portion thereof, e.g., a peptide), small molecule (of 2000 amu or less, 1000 amu or less or 500 amu or less), protein, virus, bacteria, chemical compound, mixture of chemical compounds, or an extract made from biological materials such as bacteria, plants, fungi, or animal (particularly mammalian) cells or tissues, or other biologically active agent is introduced into one or more of the biological sample holders. In one particular implementation using an array of biological sample holders, no agent is introduced into a first row of biological sample holders to preserve a control. A first agent is introduced into a second row of biological sample holders. Additional agents are added to additional rows of the array of biological sample holders.

At step 910, the fluorescence of the optical ion sensors introduced into the biological sample holders is monitored. The monitoring preferably begins prior to introduction of the agents at step 908 and continues thereafter. Changes in ion concentration resulting from the application of the voltage and/or the introduced agents are then determined based on the monitoring (step 912). By comparing the changes in ion concentration after adding an agent, one can determine whether an agent is toxic to the cells being tested. For example, if the ion concentration varies periodically in relation to an electrical stimulus prior to addition of an agent, and the addition of the agent results in a substantial change to the periodicity or amplitude of the concentration variation, one can consider the agent toxic. Alternatively, if such a change is in fact desired, for example, to treat a disease or condition, the agent might be considered a candidate therapeutic for further testing. The impact of the agent on ion flux can be compared to control agents with known impacts on voltage-gated ion channels. In one implementation, a library of agents may be tested in such a fashion as a high throughput screen to select candidate therapeutics and/or to rule out agents in the library that cause undesirable effects on voltage-gated ion channels.

EXAMPLE 1

In one particular example, a cell assay system built in accordance with principles of the invention can be used to conduct hERG screening assays. The hERG gene regulates the activity of potassium ion channels in cardiac myocyte cells. In a functioning heart, electrical voltages are generated by modified myocytes in the sinoatrial and atrioventricular nodes (pacemaking nodes). Such voltages are propagated through the heart by the action of various voltage-gated ion channels that alter the voltage gradients across cardiac cell membranes by exchanging sodium, calcium, and potassium ions across the cell membrane. Various agents are known to interfere with the hERG gene, or otherwise block potassium channel operation, resulting in arrhythmia and potentially heart failure. Thus, when testing various agents for toxicity, one useful test includes testing for interference with cardiac cell potassium channels.

To test for potassium channel interference, cardiac myocyte cells are provided in a monolayer adhered to a biological sample holder. A potassium selective optical ion sensor is introduced into the biological sample holder. Electrodes coupled to the optical ion sensor replicate the pacemaking functionality of the sinoatrial and atrioventricular nodes. As potassium ions are passed into and out of the myocytes by potassium channels, the fluorescence of the potassium selective optical ion sensor varies in a detectable fashion.

Figure 10A:
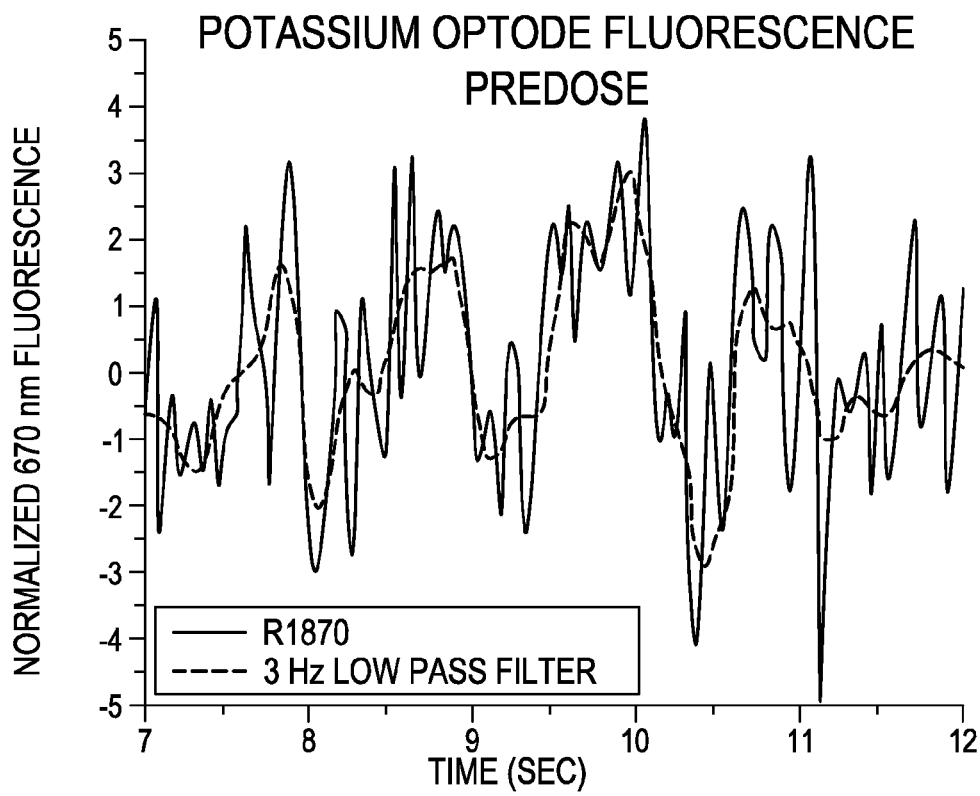
FIG. 10A-10D are graphs of experimental data derived using a potassium ion-selective optical ion sensor to monitor cardiac myocyte cells, according to an illustrative embodiment of the invention.
Figure 10B:
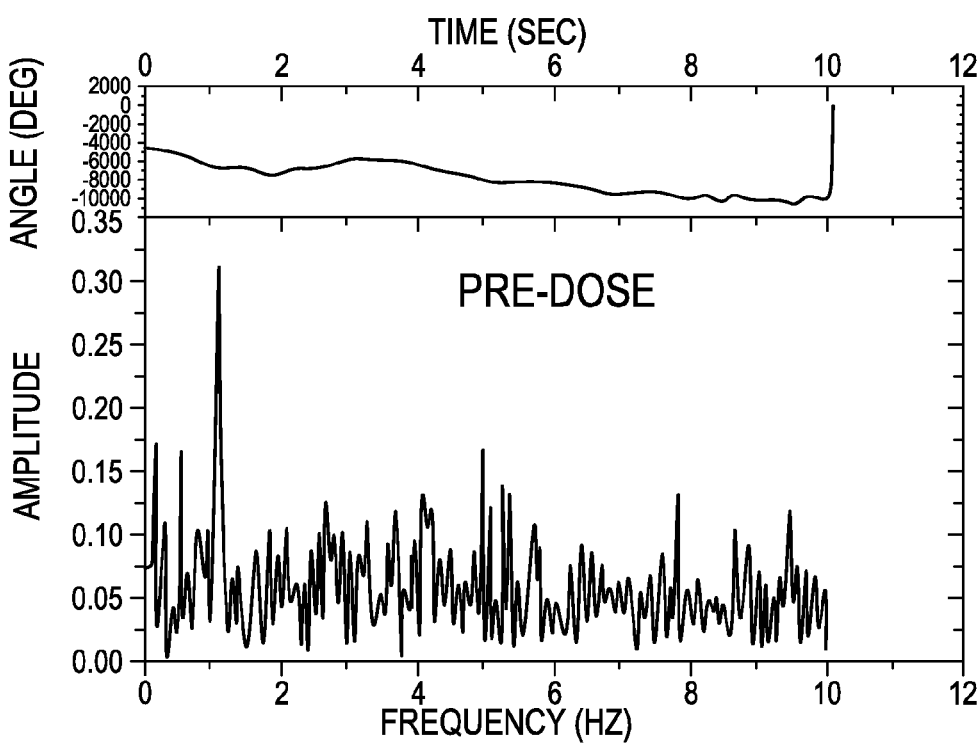

FIGS. 10A and 10B are graphs charting the intensity of potassium ion-selective optical ion sensor fluorescence monitoring the activity of myocyte cells in a biological sample holder. Voltage applied across electrodes in the biological sample holder regulates the pulse rate of the myocytes to 1.0 Hz. The graph of FIG. 10A includes normalized raw fluorescence measurements, both observed and filtered. The graph of FIG. 10B illustrates a Fast Fourier Transform breakdown of the raw data, demonstrating the fluorescence intensities by frequency. As would be expected, in the chart of 10B, a spike in intensity is visible at approximately 1.0 Hz, the pulse of the cells.

Figure 10C:
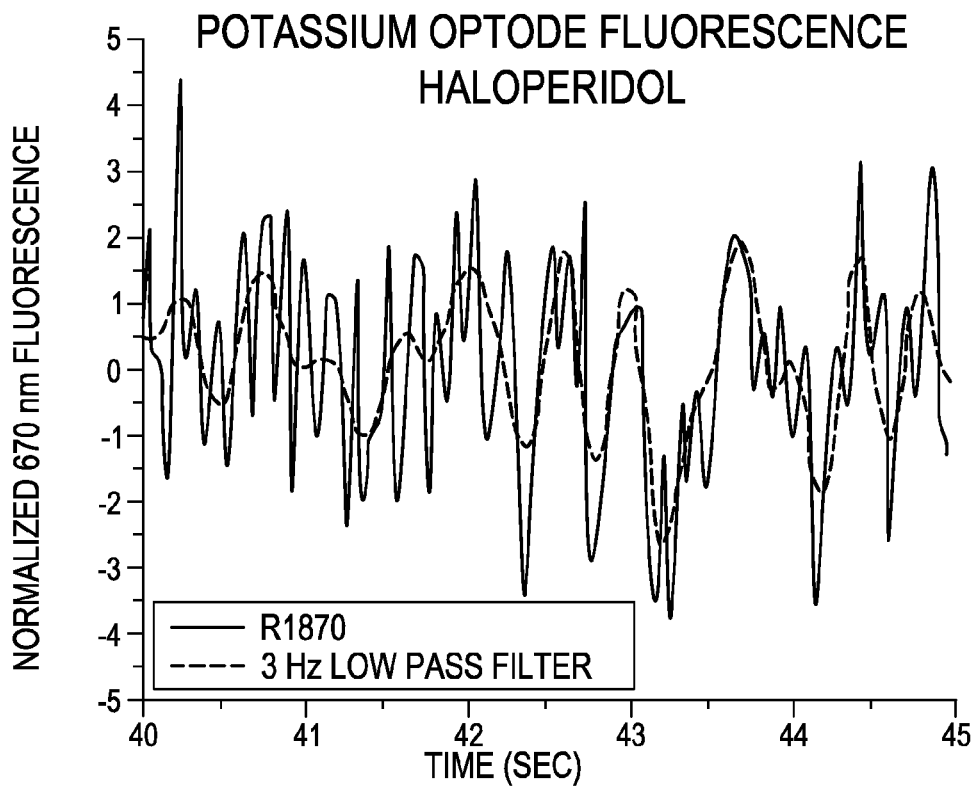
Figure 10D:
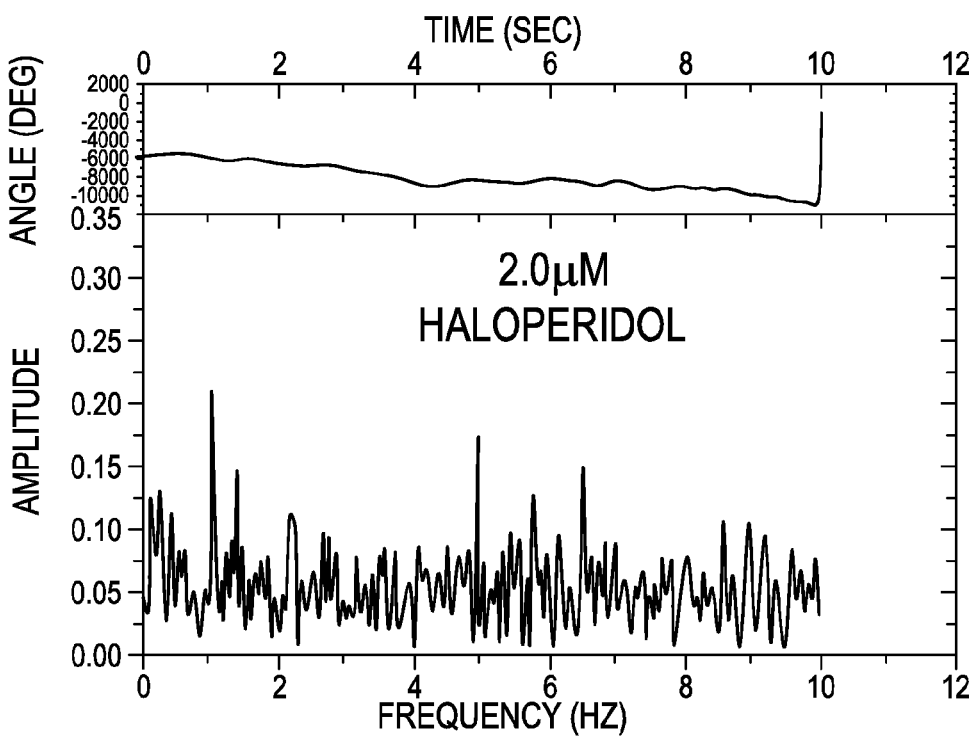

FIGS. 10C and 10D are graphs charting intensity of potassium ion-selective optical ion sensor fluorescence the after 2.0 µM of Haloperidol, a known potassium channel blocker, was introduced into the biological sample holder holding the myocyte cells. The intensity of fluorescence oscillations at 1.0 Hz, the pulse of the myocyte cells, is reduced by 30% in FIG. 10D in comparison to FIG. 10B, providing evidence of the incapacitation of potassium channels. That is, with each beat, the change of potassium concentrations in the environment outside of the myocyte cells exposed to Haloperidol is 30% less than observed with cells not exposed to the agent.

EXAMPLE 2

Figure 11A:
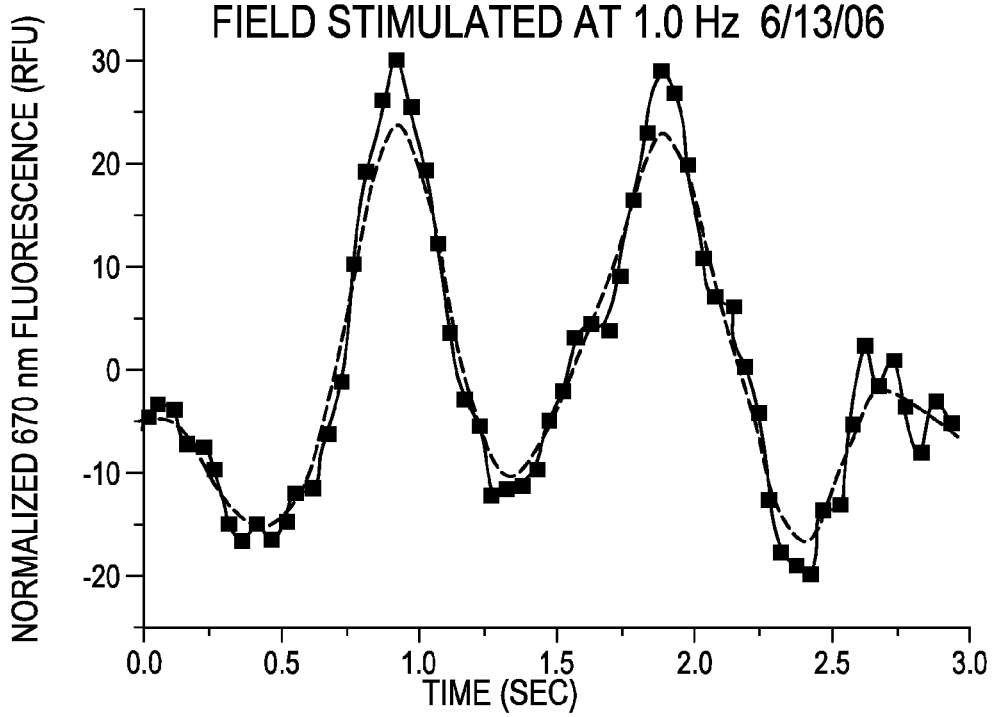
FIGS. 11A and 11B are graphs of experimental fluorescence data observed from sodium ion-selective optical ion sensor particles introduced into the interior of HL-1 cardiac cells.
Figure 11B:
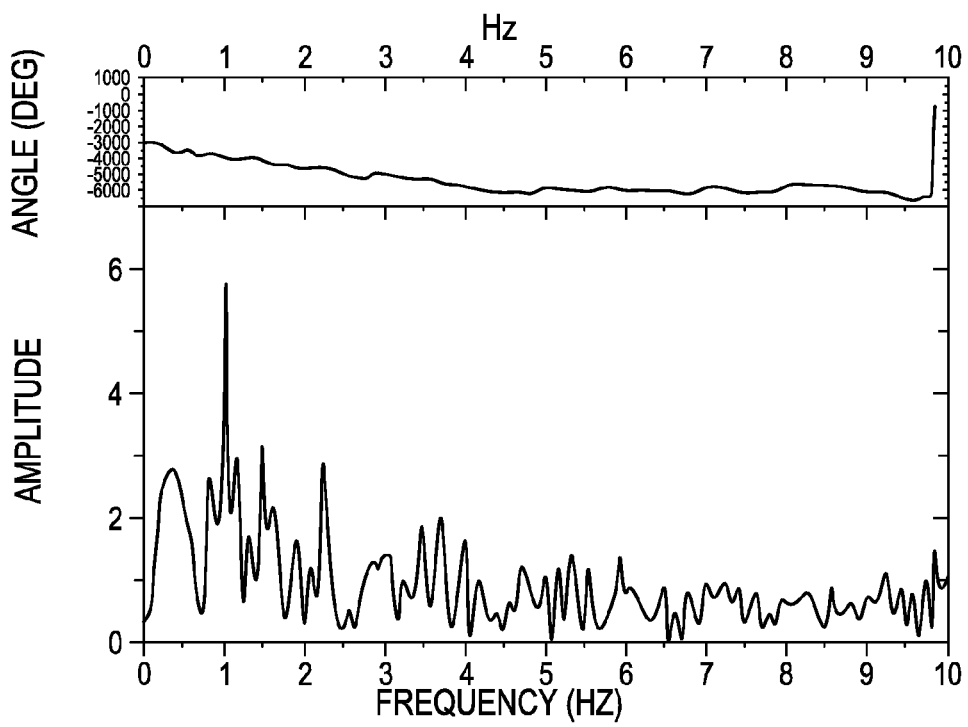

FIGS. 11A and 11B are charts depicting fluorescence data observed from sodium ion selective optical ion sensor particles introduced into the interior of HL-1 cardiac cells. Electrodes energized at a frequency of 1.0 Hz stimulate the cells. As the cells beat, sodium channels in the cells open and close, allowing sodium ions to move in and out of the cells. As the sodium concentration in the intracellular environment changes, the fluorescence of the optical ion sensor changes. FIG. 11A illustrates the averaged raw and filtered normalized fluorescence data indicative of sodium concentration in the HL-1 cells. FIG. 11B illustrates the fluorescence oscillation amplitude by frequency.

The optical ion sensors used to obtain the experimental data for FIGS. 10A-10D and FIGS. 11A and 11B fluoresce primarily at a wavelength of 670 nm. To simultaneously observe extracellular potassium and intracellular sodium, the potassium-selective optical ion sensors can be formulated with chromionophores that fluoresce at a different wavelength than the chromionophores used in the sodium-selective optical ion sensors. Similar evaluations can be carried out to determine the effect of various agents on the calcium and sodium channels of neurons.

Additional Applications

The Examples described above relate primarily to using electrodes to pace electrically excitable cells and observing the resulting activity of voltage-gated ion channels in those cells. The systems and methods described above can also be used to evaluate the activity of voltage-gated ion channels in cells which are not paced. For example, the electrodes, in one implementation can apply a DC voltage to cells in a biological sample holder to force and hold a voltage-gated ion channel into a desired state. The systems described above can then be used to analyze the effect of various agents on the activity of those ion channels. For example, the systems can detect whether the agents prevent the ion channel from opening or closing. They can also detect whether the agent makes the ion channel more or less sensitive to voltage changes.

Figure 12:
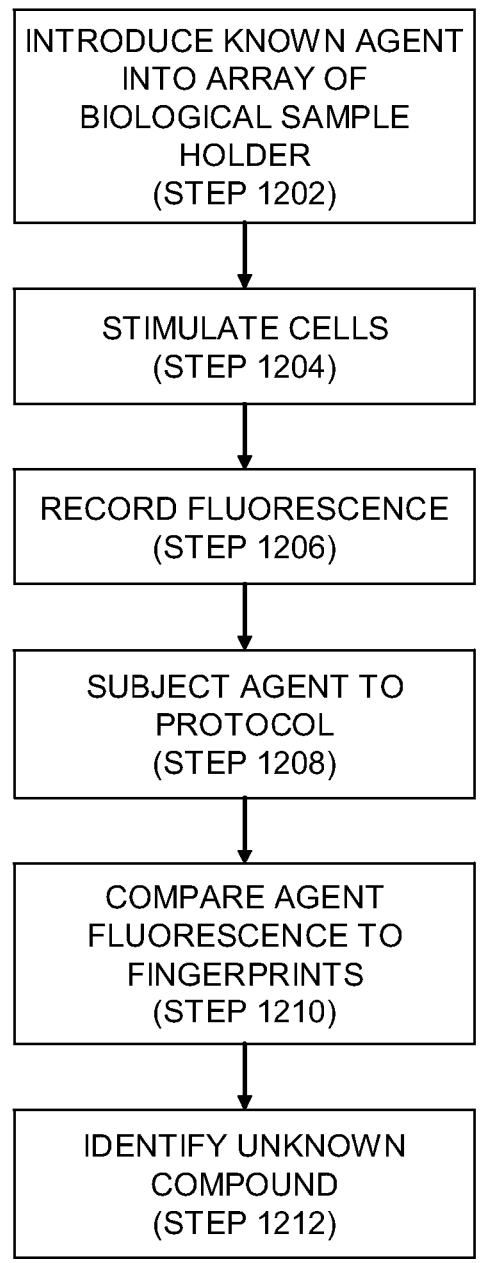
FIG. 12 is a flowchart of a method of identifying an unknown agent 1200, according to an illustrative embodiment of the invention.

FIG. 12 is a flowchart of another method of utilizing the cell assay systems described above. In particular, FIG. 12 is a flowchart of a method of identifying an unknown agent 1200. First, the impact of various agents on voltage-gated ion-channels can be catalogued and stored in a database (steps 1202-1206). For example, each agent in a library of known agents processed according to a predetermined protocol. Each agent is introduced into an array of biological sample holders holding one or more types of cells (step 1202). The cells are then electrically stimulated according to a predetermined protocol (step 1204) and the resulting fluorescence of the optical ion sensors in the biological sample holders is recorded and catalogued (step 1206). This record of fluorescence serves as a fingerprint for the agent. To identify an unknown agent (steps 1208-1212), the agent is subjected to the same protocol used to obtain the fluorescence fingerprints used populate the database (step 1208). The resultant fluorescence of the optical ion sensors monitoring the effect of the agent on the cells in the array is then compared with the fingerprints of known agents (step 1210) to identify the unknown agent (step 1212).

Additional applications and protocols for analyzing ion-channel activity are described in U.S. Pat. No. 6,969,449, the entirety of which is incorporated by reference. Such protocols can be readily adapted for use with the optical ion sensors and cell assay systems described herein.

The invention may be embodied in other specific forms without departing from the spirit or essential characteristics thereof. The forgoing embodiments are therefore to be considered in all respects illustrative, rather than limiting of the invention.

What is claimed is:

1. A method of conducting a biological assay comprising:
introducing a polymer-based optical ion sensor into a cell in a biological sample holder, wherein the optical ion sensor includes at least one ionophore for selectively binding a predetermined ion, thereby altering a pH of the optical ion sensor, and one pH-sensitive chromionophore for optically indicating the concentration of the predetermined ion based on the pH of the optical ion sensor and the resulting fluorescence of the chromionophore;
generating an electric field across the cell;
measuring an output of a light sensor monitoring the fluorescence of the optical ion sensor in response to the generation of the electric field.

2. The method of claim 1, wherein introducing the optical ion sensor into the cell comprises introducing the optical ion sensor into the biological sample holder and subsequently electroporating the cell, thereby allowing the optical ion sensor to enter the cell.

3. The method of claim 1, wherein introducing the optical ion sensor into the cell comprises applying a compound to the optical ion sensor and subsequently introducing the optical ion sensor into the biological sample holder, wherein the compound is selected to breach a vesicle formed by the cell around the optical ion sensor.

4. The method of claim 1, comprising varying the electric field at a predetermined regular frequency.

5. The method of claim 1, wherein generating the electric field comprises applying a DC voltage to a pair of electrodes.

6. The method of claim 1, comprising introducing an agent into the biological sample holder.

7. The method of claim 6, comprising detecting a change in the output of the light sensor in response to the introduction of the agent.

8. The method of claim 7, comprising determining that the agent is toxic based on the output of the light sensor.

9. The method of claim 7, comprising detecting a nerve toxin based on the output of the light sensor.

10. The method of claim 7, comprising detecting a heart toxin based on the output of the light sensor.

11. The method of claim 7, comprising determining that the agent is a candidate for treating a condition based on the output of the light sensor.

12. The method of claim 7, comprising comparing the change in the output of the light sensor to the change of output of the light sensor caused by a plurality of known agents.

13. The method of claim 12, comprising identifying the agent based on the comparison.

14. The method of claim 1, wherein the electric field is generated, at least in part, by an electrode coupled to a post positioned in the biological sample holder.

15. The method of claim 1, comprising forming a cell monolayer on the interior of the biological sample holder, wherein the cell monolayer includes the cell into which the optical ion sensor is introduced.

16. The method of claim 1, comprising introducing a second optical ion sensor into the biological sample holder to remain outside of the cell.

17. The method of claim 16, comprising comparing the fluorescence of the optical ion sensor introduced into the cell to the fluorescence of the second optical ion sensor.

18. The method of claim 17, wherein the optical ion sensor introduced into the cell includes a chromionophore selected to fluoresce at a first frequency and the second optical ion sensor includes a chromionophore selected to fluoresce at a second frequency distinguishable from the first frequency.

19. The method of claim 18, wherein the optical ion sensor introduced into the cell includes the same ionophore as is included in the second optical ion sensor, the method further comprising evaluating the comparison to determine a difference in ion concentration across a cell membrane.

20. The method of claim 18, wherein the ionophore included in the optical ion sensor introduced into the cell selectively binds a first ion and the ionophore included in the second optial sener slectively blinds a second, different ion.

21. The method of claim 16, wherein the first ion sensor comprises a sodium-selective optical ion sensor.

22. The method of claim 21, wherein the optical ion sensor comprises a potassium-selective optical ion sensor, and the cell comprises a cardiac cell.

23. The method of claim 21, wherein the second optical ion sensor comprises a calcium-selective optical ion sensor, and the cell comprises a neuron.

24. The method of claim 1, wherein the optical ion sensor comprises a chloride-selective optical ion sensor.

* * * * *